United States Patent
Siede

(10) Patent No.: US 10,662,405 B2
(45) Date of Patent: May 26, 2020

(54) **TECHNOLOGY TO IDENTIFY *CANDIDA AURIS***

(71) Applicant: Santa Fe BioLabs LLC, Fort Worth, TX (US)

(72) Inventor: Wolfram Siede, Benbrook, TX (US)

(73) Assignee: Santa Fe BioLabs LLC, Fort Worth, TX (US)

( * ) Notice: Subject to any disclaimer, the term of this patent is extended or adjusted under 35 U.S.C. 154(b) by 0 days.

(21) Appl. No.: 16/133,815

(22) Filed: Sep. 18, 2018

(65) Prior Publication Data

US 2019/0338241 A1    Nov. 7, 2019

Related U.S. Application Data

(60) Provisional application No. 62/667,534, filed on May 6, 2018.

(51) Int. Cl.
*C12Q 1/00* (2006.01)
*C12N 1/16* (2006.01)

(52) U.S. Cl.
CPC ............ *C12N 1/16* (2013.01); *C12N 2500/32* (2013.01); *C12N 2500/34* (2013.01); *C12N 2500/74* (2013.01)

(58) Field of Classification Search
CPC ...................................................... C12N 1/16
See application file for complete search history.

(56) References Cited

U.S. PATENT DOCUMENTS

2015/0299647 A1* 10/2015 Akada ...................... C12N 1/16
435/29

FOREIGN PATENT DOCUMENTS

| CN | 106748240 A | * | 5/2017 | ............... C05G 3/00 |
| JP | 43020720 B | * | 9/1968 | |

OTHER PUBLICATIONS

European Centre for Disease Prevention and Control, Candida auris in Healthcare Settings—Europe (Dec. 19, 2016), available at https://ecdc.europa.eu/sites/portal/files/media/en/publications/Publications/Candida-in-healthcare-settings_19-Dec-2016.pdf.
A. Chowdhary et al., Candida auris: a Rapidly Emerging Cause of Hospital-Acquired Multidrug-Resistant Fungal Infections Globally, 13(5) PLoS Pathogens e1006290 (May 18, 2017), available at http://journals.plos.org/plospathogens/article?id=10.1371/journal.ppat.1006290.
C.J. Clancy and M.H. Nguyen, Emergence of Candida auris: An International Call to Arms, 64 Clinical Infectious Diseases 141-143 (Jan. 2017), available at https://doi.org/10.1093/cid/ciw696.
M. Bougnoux et al., Healthcare-Associated Fungal Outbreaks: New and Uncommon Species, New Molecular Tools for Investigation and Prevention, 7:45 Antimicrobial Resistance & Infection Control (Mar. 27, 2018), available at https://doi.org/10.1186/s13756-018-0338-9.
S. Schelenz et al., First Hospital Outbreak of the Globally Emerging Candida auris in a European Hospital, 5:35 Antimicrobial Resistance & Infection Control (Oct. 19, 2016), available at https://doi.org/10.1186/s13756-016-0132-5.
A. Chakrabarti et al., Incidence, Characteristics and Outcome of ICU-Acquired Candidemia in India, 41 Intensive Care Medicine 285-295 (Feb. 2015), available at https://link.springer.com/article/10.1007/s00134-014-3603-2.
S. E. Morales-López et al., Invasive Infections with Multidrug-Resistant Yeast Candida auris, Colombia, 23 Emerging Infectious Diseases 162-164 (Jan. 2017), available at. https://dx.doi.org/10.3201/eid2301.161497.
S.R. Lockhart et al., Simultaneous Emergence of Multidrug-Resistant Candida auris on 3 Continents Confirmed by Whole-Genome Sequencing and Epidemiological Analyses, 64 Clinical Infectious Diseases 134-140 (Jan. 2017), available at https://doi.org/10.1093/cid/ciw691.
C. Piedrahita et al., Environmental Surfaces in Healthcare Facilities are a Potential Source for Transmission of Candida auris and Other Candida Species, 38 Infection Control & Hospital Epidemiology 1107-1109 (Sep. 2017), available at https://doi.org/10.1017/ice.2017.127.
A. Abdolrasouli et al., In Vitro Efficacy of Disinfectants Utilised for Skin Decolonization and Environmental Decontamination During a Hospital Outbreak With Candida Auris, 60 Mycoses 758-763 (2017), available at https://doi.org/10.1111/myc.12699.
S. Kathuria et al., Multidrug-Resistant Candida auris Misidentified as Candida haemulonii: Characterization by Matrix-Assisted Laser Desorption Ionization—Time of Flight Mass Spectrometry and DNA Sequencing and Its Antifungal Susceptibility Profile Variability by Vitek 2, CLSI Broth Microdilution, and Etest Method, 53 Journal of Microbiology 1823-1830 (Jun. 2015), available at http://jcm.asm.org/content/53/6/1823.full.pdf+html.
J.L. Cadnum et al., Effectiveness of Disinfectants Against Candida auris and Other Candida Species, 38 Infection Control & Hospital Epidemiology 1240-1243 (Oct. 2017), available at https://doi.org/10.1017/ice.2017.162.

(Continued)

*Primary Examiner* — Albert M Navarro
*Assistant Examiner* — Mark Navarro
(74) *Attorney, Agent, or Firm* — D. Tiller Law PLLC; Donald Tiller

(57) ABSTRACT

A system for identifying *Candida auris* is disclosed. The system has two aspects. The first is a positive selection of *C. auris* based on *C. auris*'s distinctive resistance to quaternary ammonium compounds (especially at elevated incubation temperatures). The second is a negative selection of *C. auris* based on *C. auris*'s distinctive sensitive to tert-Butyl-hydroperoxide. *C. auris* can be identified in a sample through use of a positive-selection culture medium, which fosters *C. auris* colony growth while suppressing growth of other yeasts. The isolate can be confirmed as *C. auris* through use of a negative-selection culture medium, which suppresses *C. auris* colony growth while permitting growth of other yeasts.

18 Claims, 18 Drawing Sheets

(56) References Cited

OTHER PUBLICATIONS

Sexton, D.J. et al. (2018) Direct Detection of Emergent Fungal Pathogen Candida auris in Clinical Skin Swabs by SYBR Green-Based Quantitative PCR Assay. J Clin Microbiol 56 (12).
Jeffery-Smith, A. et al. (2018) Candida auris: a Review of the Literature. Clin Microbiol Rev 31 (1).
Suleyman, G. and Alangaden, G.J. (2016) Nosocomial Fungal Infections: Epidemiology, Infection Control, and Prevention. Infect Dis Clin North Am 30 (4), 1023-1052.
Walker, E. (2003) Quaternary ammonium compounds. In Handbook of Topical Antimicrobials—Industrial Applications in Consumer Products and Pharmaceuticals (Paulson, D. ed), pp. 99-116, Marcel Dekker, Inc.
Mizusawa, M. et al. (2017) Can Multidrug-Resistant Candida auris Be Reliably Identified in Clinical Microbiology Laboratories? J Clin Microbiol 55 (2), 638-640.

\* cited by examiner positive selection positive selection

FIG. 4

Plating Scheme B

|   | 1 | 2 |
|---|---|---|
| A | *Candida auris:* CDC-AR Bank #0381 | *Candida auris:* CDC-AR Bank #0386 |
| B | *Candida auris:* CDC-AR Bank #0382 | *Candida auris:* CDC-AR Bank #0387 |
| C | *Candida auris:* CDC-AR Bank #0383 | *Candida auris:* CDC-AR Bank #0388 |
| D | *Candida auris:* CDC-AR Bank #0384 | *Candida auris:* CDC-AR Bank #0389 |
| E | *Candida auris:* CDC-AR Bank #0385 | *Candida auris:* CDC-AR Bank #0390 |
| F |   |   | control
30°C
48 hours

Step-1 Medium
37°C
72 hours

Plating Scheme C control: YPD
30°C
48 hours control: BHI
37°C
72 hours

Step-1 Medium
37°C
72 hours

FIG. 8
Plating Scheme C

|   | 1 | 2 | 3 | 4 | 5 | 6 |
|---|---|---|---|---|---|---|
| A | *Candida auris* CDC-AR Bank #0381 | *Candida auris* CDC-AR Bank #0386 | *Candida duobus-haemulonii* CDC-AR Bank #0391 | *Kodameae ohmeri* CDC-AR Bank #0396 | *Candida haemulonii* DMS70624 | *Candida albicans* SC5314 = ATCC MYA 2876 |
| B | *Candida auris* CDC-AR Bank #0382 | *Candida auris* CDC-AR Bank #0387 | *Candida duobus-haemulonii* CDC-AR Bank #0392 | *Candida krusei* CDC-AR Bank #0397 | *Candida krusei* ATCC14243 | *Candida glabrata* CBS138 = ATCC2001 |
| C | *Candida auris* CDC-AR Bank #0383 | *Candida auris* CDC-AR Bank #0388 | *Candida haemulonii* CDC-AR Bank #0393 | *Candida lusitaniae* CDC-AR Bank #0398 | | *Candida famata* DMS3428 |
| D | *Candida auris* CDC-AR Bank #0384 | *Candida auris* CDC-AR Bank #0389 | *Candida duobus-haemulonii* CDC-AR Bank #0394 | *Saccharomyces cerevisiae* CDC-AR Bank #0399 | | *Candida parapsilosis* ATCC22019 |
| E | *Candida auris* CDC-AR Bank #0385 | *Candida auris* CDC-AR Bank #0390 | *Candida haemulonii* CDC-AR Bank #0395 | *Saccharomyces cerevisiae* CDC-AR Bank #0400 | | *Candida tropicalis* ATCC750 |
| F | | | | | | | control
30°C
48 hours

Step-1 Medium
30°C
48 hours control
37°C
48 hours

Step-1 Medium
37°C
48 hours control
30°C
48 hours

Step-2 Medium
30°C
48 hours control
37°C
48 hours

Step-2 Medium
37°C
48 hours

FIG. 13A
negative selection

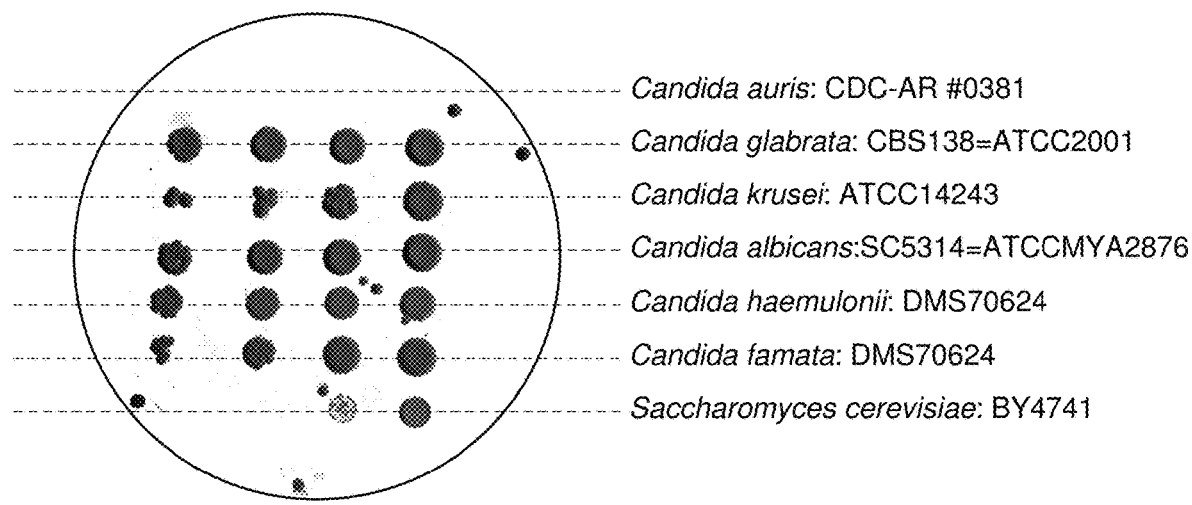

- Candida auris: CDC-AR #0381
- Candida glabrata: CBS138=ATCC2001
- Candida krusei: ATCC14243
- Candida albicans:SC5314=ATCCMYA2876
- Candida haemulonii: DMS70624
- Candida famata: DMS70624
- Saccharomyces cerevisiae: BY4741

FIG. 13B
negative selection

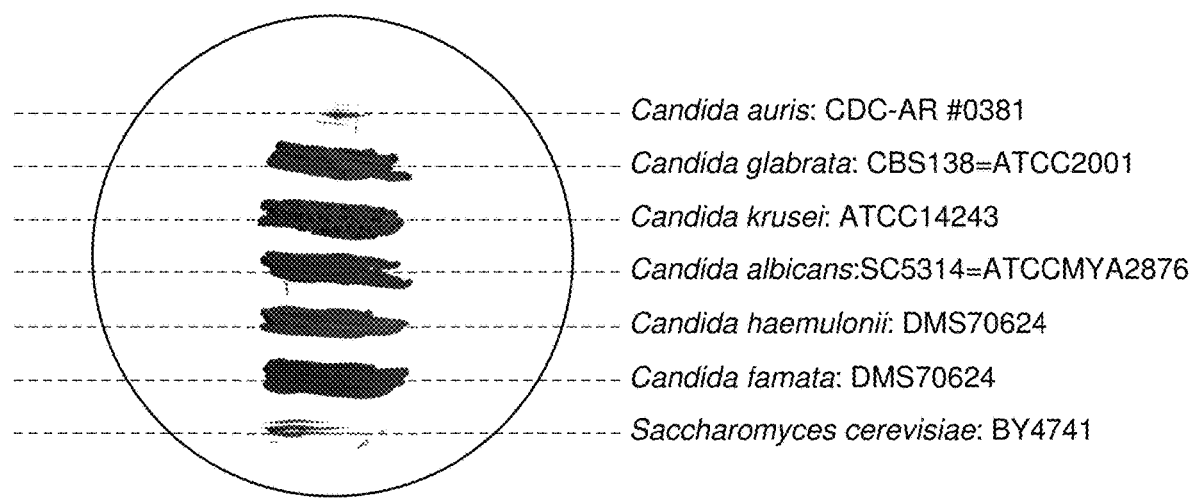

- Candida auris: CDC-AR #0381
- Candida glabrata: CBS138=ATCC2001
- Candida krusei: ATCC14243
- Candida albicans:SC5314=ATCCMYA2876
- Candida haemulonii: DMS70624
- Candida famata: DMS70624
- Saccharomyces cerevisiae: BY4741 control
30°C
24 hours tBHP Medium
30°C
24 hours

TECHNOLOGY TO IDENTIFY *CANDIDA AURIS*

CROSS-REFERENCE TO RELATED APPLICATIONS

This application claims the benefit of U.S. Provisional Application No. 62/667,534, filed on May 6, 2018, the entirety of which is hereby incorporated by reference.

BACKGROUND

This invention pertains generally to systems and methods for detecting the yeast *Candida auris* ("*C. auris*"). More specifically, the invention is directed to the composition and use of yeast growth media that selectively supports or deters the growth of *C. auris* relative to other species of fungi.

*C. auris* has emerged as a novel organism causing infections in hospital settings. It is rapidly developing into a global threat. According to the Centers for Disease Control and Prevention (CDC): "*Candida auris* is an emerging fungus that presents a serious global health threat." CDC, *Candida auris*, www.cdc.gov/fungal/diseases/candidiasis/Candida-auris.html. Within a period of only 7 years, the organism has caused healthcare-associated outbreaks in four continents. See, e.g., European Centre for Disease Prevention and Control, *Candida auris in Healthcare Settings—Europe* (Dec. 19, 2016), available at ecdc.europa.eu/sites/portal/files/media/en/publications/Publications/Candida-in-healthcare-settings_19-Dec-2016.pdf; A. Chowdhary et al., *Candida auris: a Rapidly Emerging Cause of Hospital-Acquired Multidrug-Resistant Fungal Infections Globally*, 13(5) PLoS Pathogens e1006290 (May 18, 2017), available at journals.plos.org/plospathogens/article?id=10.1371/journal.ppat.1006290; C. J. Clancy and M. N. Nguyen, *Emergence of Candida auris: An International Call to Arms*, 64 Clinical Infectious Diseases 141-143 (January 2017), available at doi.org/10.1093/cid/ciw696; M. Bougnoux et al., *Healthcare-Associated Fungal Outbreaks: New and Uncommon Species, New Molecular Tools for Investigation and Prevention*, 7:45 Antimicrobial Resistance & Infection Control (Mar. 27, 2018), available at doi.org/10.1186/s13756-018-0338-9. For example, major outbreaks were reported in Spain (33 bloodstream infections in a surgical ICU unit) and London (50 cases in a cardiothoracic center). S. Schelenz et al., *First Hospital Outbreak of the Globally Emerging Candida auris In a European Hospital*, 5:35 Antimicrobial Resistance & Infection Control (Oct. 19, 2016), available at doi.org/10.1186/s13756-016-0132-5. As of Jul. 31, 2018, there were more than 350 confirmed cases of *C. auris* infection in the US, with the majority of cases located in New York and New Jersey. CDC, *Tracking Candida auris*, www.cdc.gov/fungal/diseases/candidiasis/tracking-c-auris.html.

*C. auris* is prone to be spread in hospital settings and there are indications that it is becoming more widely established. In India, for example, *C. auris* at one point accounted for 5% of cases of candidemia acquired in intensive care units. A. Chakrabarti et al., *Incidence, Characteristics and Outcome of ICU-Acquired Candidemia In India*, 41 Intensive Care Medicine 285-295 (February 2015), available at link.springer.com/article/10.1007/s00134-014-3603-2. The species "has caused outbreaks in healthcare settings." CDC, *Candida auris*, www.cdc.gov/fungal/diseases/candidiasis/Candida-auris.html.

*C. auris* infections are dangerous and difficult to treat. *C. auris* has the potential to be multi-drug resistant—isolates have been detected that are resistant to all major classes of antifungal agents. Thus, it is difficult to treat a *C. auris* infection. CDC, *Candida auris*, www.cdc.gov/fungal/diseases/candidiasis/Candida-auris.html. Invasive infections with *C. auris* currently carry a high mortality (30-60%), even if receiving treatment. See, e.g., CDC, *Fact Sheet*, www.cdc.gov/fungal/diseases/candidiasis/c-auris-drug-resistant.html ("More than 1 in 3 patients with invasive *C. auris* infection . . . die."); S. E. Morales-López et al., *Invasive Infections with Multidrug-Resistant Yeast Candida auris, Colombia*, 23 Emerging Infectious Diseases 162-164 (January 2017), available at. dx.doi.org/10.3201/eid2301.161497; C. J. Clancy and M. H. Nguyen, *Emergence of Candida auris: An International Call to Arms*, 64 Clinical Infectious Diseases 141-143 (January 2017), available at doi.org/10.1093/cid/ciw696; S. R. Lockhart et al., *Simultaneous Emergence of Multidrug-Resistant Candida auris on 3 Continents Confirmed by Whole-Genome Sequencing and Epidemiological Analyses*, 64 Clinical Infectious Diseases 134-140 (January 2017), available at doi.org/10.1093/cid/ciw691.

Because of the danger posed by *C. auris*, early detection is important. See, e.g., CDC, *Candida auris*,www.cdc.gov/fungal/diseases/candidiasis/Candida-auris.html ("it is important to quickly identify *C. auris* in a hospitalized patient so that healthcare facilities can take special precautions to stop its spread"); European Centre for Disease Prevention and Control, *Candida auris in Healthcare Settings—Europe* (Dec. 19, 2016), available at ecdc.europa.eu/sites/portal/files/media/en/publications/Publications/Candida-in-healthcare-settings_19-Dec-2016.pdf. The need for early detection in a patient or a hospital environment is even more urgent since *C. auris* can persist on moist or dry surfaces in a hospital environment for at least 7-30 days. C. Piedrahita et al., *Environmental Surfaces in Healthcare Facilities are a Potential Source for Transmission of Candida auris and Other Candida Species*, 38 Infection Control & Hospital Epidemiology 1107-1109 (September 2017), available at doi.org/10.1017/ice.2017.127; A. Abdolrasouli et al., *In Vitro Efficacy of Disinfectants Utilised for Skin Decolonization and Environmental Decontamination During a Hospital Outbreak With Candida Auris*, 60 Mycoses 758-763 (2017), available at doi.org/10.1111/myc.12699.

Unfortunately, *C. auris* is not easy to identify and is prone to misdiagnosis by conventional methods. CDC, *Candida auris*, cdc.gov/fungal/diseases/candidiasis/Candida-auris.html. The CDC note that *C. auris* "is difficult to identify with standard laboratory methods, and it can be misidentified in labs without specific technology." Id. Indeed, traditional detection methods result in "common misidentifications based on the identification method used." CDC, *Recommendations for Identification of Candida auris*, www.cdc.gov/fungal/diseases/candidiasis/recommendations.html; see also, S. Kathuria et al., *Multidrug-Resistant Candida auris Misidentified as Candida haemulonii: Characterization by Matrix-Assisted Laser Desorption Ionization—Time of Flight Mass Spectrometry and DNA Sequencing and Its Antifungal Susceptibility Profile Variability by Vitek 2, CLSI Broth Microdilution, and Etest Method*, 53 Journal of Microbiology 1823-1830 (June 2015), available at jcm.asm.org/content/53/6/1823.full.pdf+html; A. Chowdhary et al., *Candida auris: a Rapidly Emerging Cause of Hospital-Acquired Multidrug-Resistant Fungal Infections Globally*, 13(5) PLoS Pathogens e1006290 (May 18, 2017), available at journals.plos.org/plospathogens/article?id=10.1371/journal.ppat.1006290.

The state-of-the-art yeast-detection systems either fail to adequately identify *C. auris* (because of common misidentifications) or they are expensive and cumbersome to use. They fail to timely identify the presence—and threat—of *C. auris*. The failings in the detection systems and the multi-drug-resistant nature of *Candida auris* threaten dangerous outbreaks of *Candida auris* infections. Currently, no simple detectable markers for the presence of *C. auris* are known. In the near future, PCR-based methods may be available to detect the presence of *C. auris* DNA quickly and accurately. However, this method does not allow the distinction between dead and viable (i.e., colony-forming) cells and does not provide the cells for further investigation, e.g. analysis of their drug resistance (which is important for therapy) or their genetic makeup.

Accordingly, there is a need for a means to accurately and timely identify viable *C. auris* and to isolate those cells for further study.

SUMMARY

The present invention is directed to systems and methods to identify and isolate viable *C. auris* based on *C. auris*'s distinctive and tailorable sensitivity to certain compounds. As discovered as part of this research, *C. auris* generally shows a higher resistance to Quaternary Ammonium Compound ("QACs") than do other yeasts. If compared to most other yeasts, the difference in resistance increases at higher temperatures (e.g., the difference in resistance is greater at 37° C.-38.5° C. than it is at 30° C.). Thus, a QAC-containing culture medium generally allows the growth of *C. auris* cells into colonies while suppressing the growth of other yeast colonies, and thereby acts as a positive-selection system for *C. auris*. The yeast-supplement mixture in the culture medium may be formulated to change *C. auris*'s resistance to a QAC relative to other yeasts' resistance to a QAC. For many yeasts, a nutritionally-poor-and-defined yeast-supplement mixture will increase *C. auris*'s relative resistance compared to a nutritionally-rich-and-complex yeast-supplement mixture. *C. auris* also generally shows a lower resistance to tert-Butyl-hydroperoxide ("tBHP") than do other yeasts. Thus, a tBHP-containing culture medium generally suppresses growth of *C. auris* colonies while allowing the growth of other yeast colonies, and thereby acts as negative-selection system for *C. auris*.

In one aspect of the invention, a *C. auris* positive-selection culture medium includes a QAC, a sugar, and a yeast supplement. Exemplary QACs include cetylpyridinium chloride, benzalkonium chloride, benzethonium chloride, and tetradecyltrimethylammonium bromide. The culture medium may include a solidifying agent such as agar, when solid-medium-based assays (e.g., plate assays) are desired. The culture medium may include a nutritionally poor (without amino acids) and defined yeast-supplement mixture or it may include a nutritionally rich (with amino acids) and complex yeast-supplement mixture. The yeast-supplement mixture may be used to tailor the relative sensitivity of *C. auris* to the QAC (relative to other organisms). An antibiotic may be included in the medium. The positive-selection culture medium may be used for culturing *C. auris* while suppressing the growth of other microorganisms.

In another aspect of the invention, a method for detecting *C. auris* includes inoculating a QAC-based *C. auris* positive-selection culture medium with a sample and incubating the inoculated medium at a temperature above the standard yeast-incubation temperature (e.g., ~36.5° C.-39.0° C. versus the standard ~30° C.). The growth of cultures in such an assay suggests the presence of *C. auris* in the sample.

In another aspect of the invention, a method for detecting *C. auris* includes use of two different positive-selection media. The method includes inoculating a QAC-based *C. auris* positive-selection culture medium containing a nutritionally poor yeast supplement with a sample, incubating the inoculated medium at a temperature above the standard yeast-incubation temperature, collecting a sample from cultures grown on the incubated medium, inoculating a QAC-based *C. auris* positive-selection culture medium containing a nutritionally rich yeast supplement with the culture sample, incubating the inoculated medium at a temperature above the standard yeast-incubation temperature. The growth of cultures on the second incubated medium (the nutritionally rich medium) in such an assay suggests the presence of *C. auris* in the sample.

In another aspect of the invention, a method for detecting *C. auris* includes combining a *C. auris* positive-selection-culture-medium-based assay with a *C. auris* negative-selection-culture-medium-based assay. The positive-selection medium includes a QAC. The negative selection medium includes tBHP. The positive-selection culture medium supports the growth of *C. auris* while suppressing the growth of other microorganisms. The negative-selection culture medium suppresses the growth of *C. auris* while supporting the growth of other microorganisms. Growth of yeast cultures on a positive-selection culture medium after incubation at an elevated temperature (relative to the standard yeast-incubation temperature) suggests the presence of *C. auris*. Growth of yeast cultures on a negative-selection culture medium after incubation at the standard yeast-incubation temperature suggests the absence of *C. auris*. The assays may be performed on a common sample (e.g., a wipe of a surface in a hospital) in parallel: cultures on the positive-selection medium combined with no cultures on the negative-selection medium suggests the presence of *C. auris*. The assays may also be performed in sequence, with samples from the cultures grown on a positive-selection medium being used to inoculate a negative selection medium (perhaps with intervening culturing on a nonselective culture medium or a different positive-selection culture medium). The combination of positive-selection and negative-selection assays may provide more certain identification of *C. auris* than either assay alone.

BRIEF DESCRIPTION OF THE DRAWINGS

These and other features, aspects, and advantages of the present invention will become better understood with reference to the following description, appended claims, and accompanying drawings where:

FIG. 1 depicts the plating scheme for the suspension-based plate assays depicted in FIGS. 2 and 13A.

FIG. 2 depicts plate assays for various yeasts using culture media containing different amounts of a Quaternary Ammonium Compound (QAC, cetylpyridinium chloride in this example) and using different incubation temperatures.

FIG. 3 depicts a comparison between a plate assay using the nonselective standard Sabouraud-dextrose culture medium (left) and using an exemplary QAC-based positive-selection culture medium (right).

FIG. 4 depicts the plating scheme for the assays depicted in FIGS. 5A and 5B.

FIGS. 5A-5B depict plate assays for 25-day-old *C. auris* cells using a standard Sabouraud-dextrose culture medium (FIG. 5A) and a QAC-based positive-selection medium configured to support old *C. auris* cells (FIG. 5B).

FIG. 8 depicts the plating scheme for the assays depicted in FIGS. 9A-13B.

FIGS. 13A-13B depict plate assays for a variety of organisms using a standard, nonselective, Sabouraud-dextrose culture medium (FIG. 13A) and a negative-selection culture medium containing tert-butyl-hydroperoxide (tBHP) (FIG. 13B).

DETAILED DESCRIPTION

Figure 1:
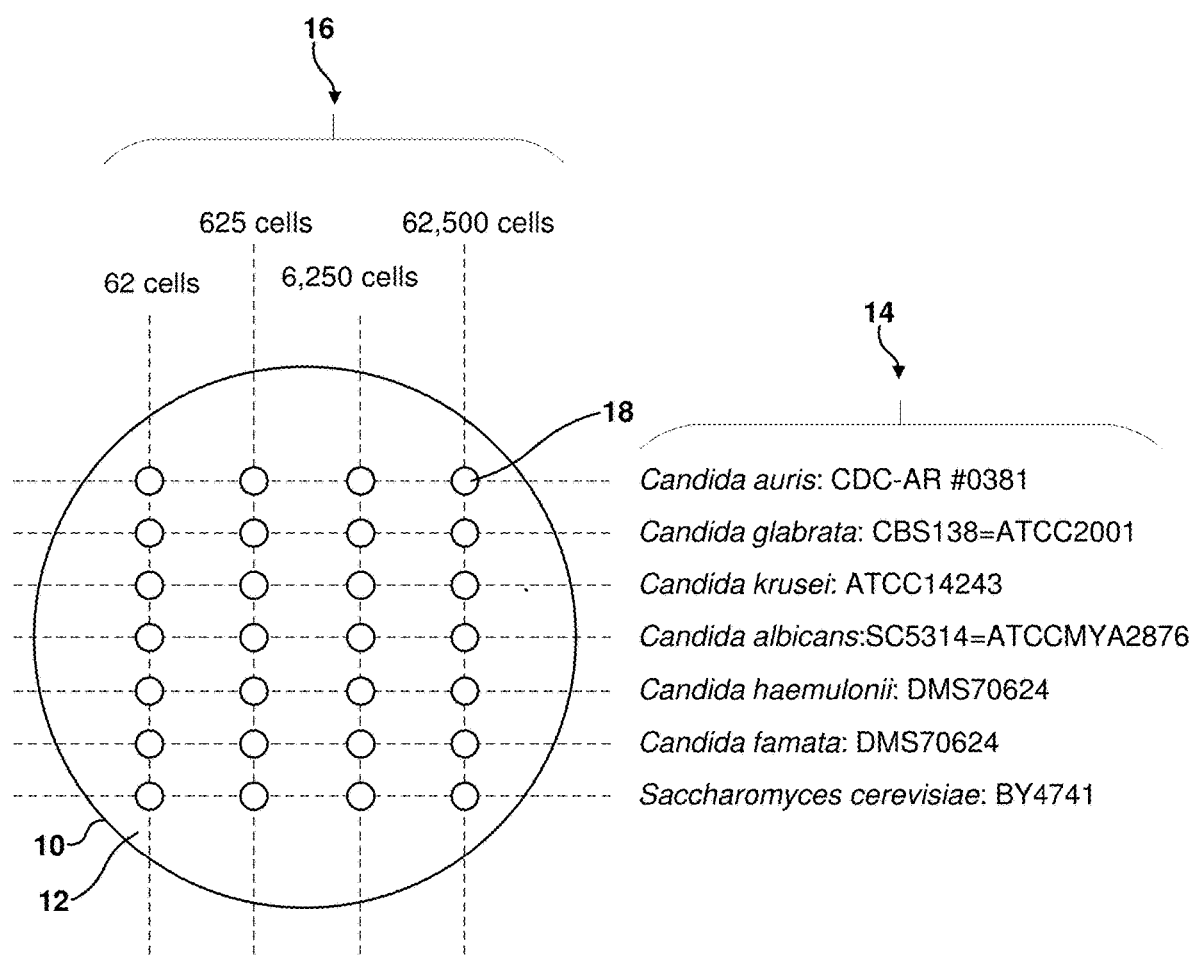

In the summary above, and in the description below, reference is made to particular features of the invention in the context of exemplary embodiments of the invention. The features are described in the context of the exemplary embodiments to facilitate understanding. But the invention is not limited to the exemplary embodiments. And the features are not limited to the embodiments by which they are described. The invention provides a number of inventive features which can be combined in many ways, and the invention can be embodied in a wide variety of contexts. Unless expressly set forth as an essential feature of the invention, a feature of a particular embodiment should not be read into the claims unless expressly recited in a claim.

Except as explicitly defined otherwise, the words and phrases used herein, including terms used in the claims, carry the same meaning they carry to one of ordinary skill in the art as ordinarily used in the art.

Because one of ordinary skill in the art may best understand the structure of the invention by the function of various structural features of the invention, certain structural features may be explained or claimed with reference to the function of a feature. Unless used in the context of describing or claiming a particular inventive function (e.g., a process), reference to the function of a structural feature refers to the capability of the structural feature, not to an instance of use of the invention.

Except for claims that include language introducing a function with "means for" or "step for," the claims are not recited in so-called means-plus-function or step-plus-function format governed by 35 U.S.C. § 112(f). Claims that include the "means for [function]" language but also recite the structure for performing the function are not means-plus-function claims governed by § 112(f). Claims that include the "step for [function]" language but also recite an act for performing the function are not step-plus-function claims governed by § 112(f).

Except as otherwise stated herein or as is otherwise clear from context, the inventive methods comprising or consisting of more than one step may be carried out without concern for the order of the steps.

The terms "comprising," "comprises," "including," "includes," "having," "haves," and their grammatical equivalents are used herein to mean that other components or steps are optionally present. For example, an article comprising A, B, and C includes an article having only A, B, and C as well as articles having A, B, C, and other components. And a method comprising the steps A, B, and C includes methods having only the steps A, B, and C as well as methods having the steps A, B, C, and other steps.

Terms of degree, such as "substantially," "about," and "approximately," are used herein to denote features that satisfy their technological purpose equivalently to a feature that is "exact." For example, a component A is "substantially" perpendicular to a second component B if A and B are at an angle such as to equivalently satisfy the technological purpose of A being perpendicular to B.

Except as otherwise stated herein, or as is otherwise clear from context, the term "or" is used herein in its inclusive sense. For example, "A or B" means "A or B, or both A and B."

In the culture assays depicted herein, (e.g., FIGS. 2, 3, 5A, 5B, 7A, 7B, 7C, 9A, 9B, 10A, 10B, 11A, 11B, 12A, 12B, 13A, 13B,) a dark spot denotes the presence of a colony. Larger spots depict larger colonies. More spots depict more colonies. The density or overlap of colonies often results in a single spot.

The invention is premised on the discovery that *C. auris* has two distinctive phenotypes: First, *C. auris* is relatively more resistant to quaternary ammonium compounds ("QACs" or "quats") when compared to other yeasts. This relative resistance increases at higher temperatures (other yeasts show a decreased resistance at higher temperature while *C. auris* remains approximately the same). And a difference in relative sensitivity to a particular QAC between *C. auris* and another yeast can be enhanced by choosing a particular kind of growth-factor supplement (for example, Yeast Nitrogen Base vs. peptone). Second, *C. auris* is relatively less resistant to tert-butyl-hydroperoxide ("tBHP") when compared to other yeasts. Utilizing these relative sensitivities, identification of *C. auris* is improved through use of a culture medium that allows *C. auris* growth while suppressing other yeasts ("positive selection") and a culture medium that suppresses *C. auris* growth while allowing the growth of other yeasts ("negative selection").

Positive-Selection System: *C. auris* has a high degree of relative resistance towards QACs, such as cetylpyridinium chloride. The same is true for *C. haemulonii* which (together with *C. lusitaniae* and *C. krusei*) is the closest relative to *C. auris*. The closely-related *Candida* species can be distinguished, however, by their differential QAC resistance at higher-than-standard yeast incubation temperatures (preferably in the range of 37° C.-38.5° C. vs the standard 30° C.). Besides cetylpyridinium chloride, other QACs, including benzalkonium chloride, benzethonium chloride, and tetradecyltrimethylammonium bromide were successfully used to differentiate *C. auris* from other *Candida* species. As an added benefit, growth of many bacteria and molds is suppressed at the applied QAC concentrations. This makes this system an appealing choice for positive selection of *C. auris* within a sample containing mixed microbial species (e.g. a sample wiped from human skin).

Discriminating *Candida* species based on their relative sensitivity to QACs is a novel approach to identifying *C. auris*. QACs are known to be relatively ineffective in suppressing or killing *Candida* species. Using short-term exposure, activity of QACs has been described as generally weak in various *Candida* species. See, e.g., J. L. Cadnum et al., *Effectiveness of Disinfectants Against Candida auris and Other Candida Species*, 38 Infection Control & Hospital Epidemiology 1240-1243 (October 2017), available at doi.org/10.1017/ice.2017.162. But differential sensitivity of colony formation ability among different *Candida* species to QACs added to growth media is largely unexplored. Using this discriminating phenotype is a novel and effective way to identify *C. auris*. Further, using the temperature and growth factor supplement dependence of the relative sensitivity to QACs is a novel and effective way to identify *C. auris*. This relative sensitivity is the basis for positive selection media for *C. auris*.

Figure 2:
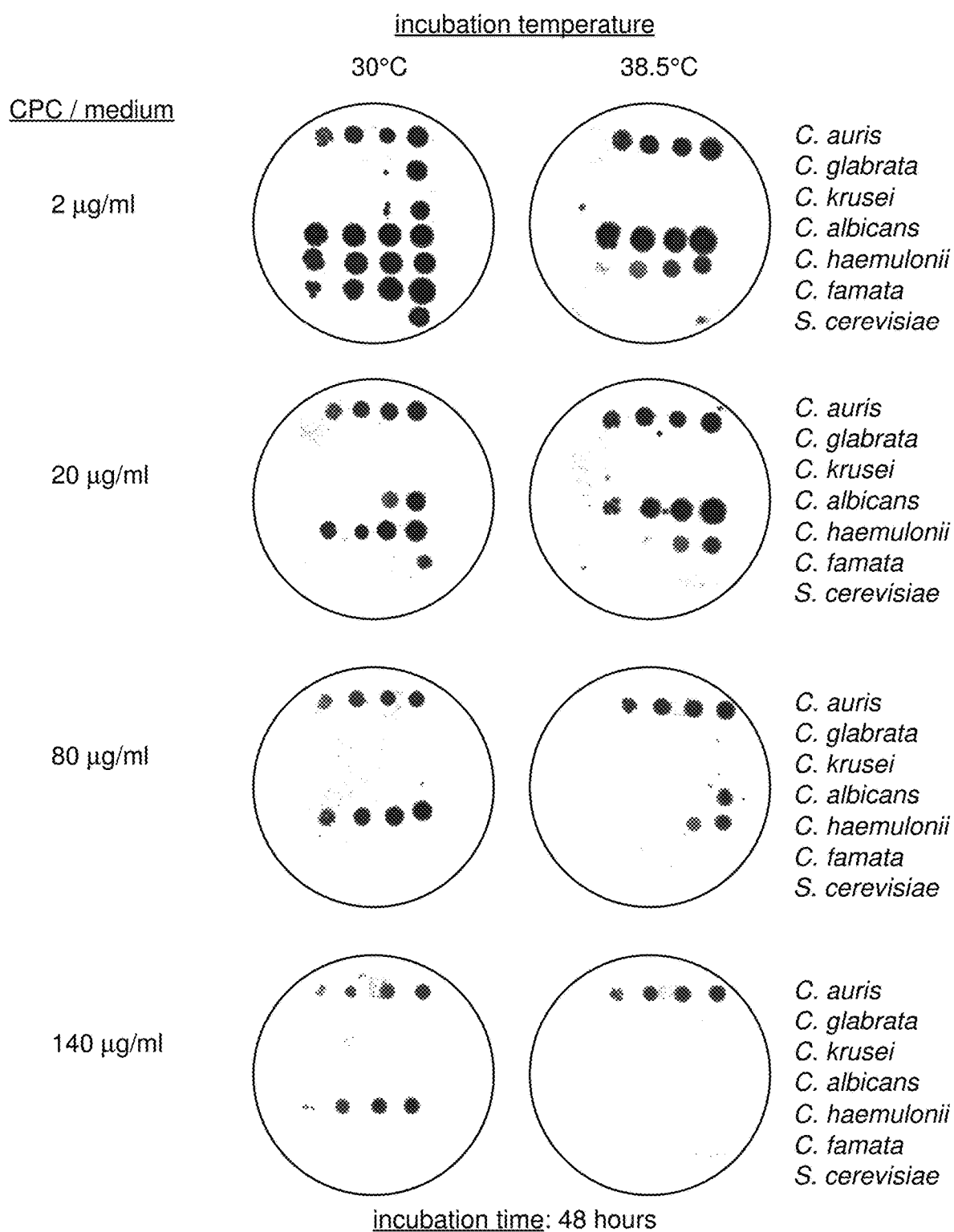

FIG. 2 illustrates *C. auris*'s relative resistance to cetylpyridinium chloride. The figure depicts eight plates containing four different culture mediums that differ with respect to the concentration of cetylpyridinium chloride in the medium. Each plate includes seven different yeasts (*Candida albicans, Candida glabrata, Candida krusei, Candida auris, Candida haemulonii, Candida famata*, and *Saccharomyces cerevisiae*) at four different calculated cell counts (62, 625, 6,250, 62,500, with the uncertainty inherent in the calculation). Four of the yeast-containing plates (one of each culture medium) were incubated at 30° C. and the other four (one of each culture medium) were incubated at 38.5° C.

The plating scheme for the FIG. 2 assay is illustrated in FIG. 1. Drops of various yeast suspensions are placed on a culture medium 12 in a plate 10. The drops contain yeasts (*Candida albicans, Candida glabrata, Candida krusei, Candida auris, Candida haemulonii, Candida famata*, and *Saccharomyces cerevisiae*) as listed on the vertical axis 14. The drops contain different calculated cell counts (62, 625, 6,250, 62,500) as listed on the horizontal axis 16. The dashed lines are there to show the intersection of yeast and cell count for a particular drop. For example, the drop 18 at the intersection of *C. auris* and 62,500 indicates that a drop with 62,500 cells of *C. auris* was placed on the medium 12 at that spot.

Yeasts were first streaked on Sabouraud-dextrose agar plates and pre-grown at 30° C. for 72 hours. Suspensions were made and adjusted to $2.5 \times 10^7$ cells per ml and subjected to serial 1:10 dilutions. Drops were placed on solid agar plates of Sabouraud dextrose (4% dextrose and 10 g/l peptone) which contained various amounts of cetylpyridinium chloride that were added after autoclaving from a 2% stock solution in isopropanol.

As shown, after 48 hours of incubation at 30° C., *C. glabrata, C. krusei*, and *S. cerevisiae* are most sensitive whereas *C. auris* and *C. haemulonii* are the most resistant species. As the amount of cetylpyridinium chloride in the medium increases (top to bottom in the figure), all but *C. auris* and *C. haemulonii* are suppressed. These two species cannot be distinguished one from the other on the data presented. Notably, *C. auris* is frequently misidentified as *C. haemulonii* in the VITEK identification system. S. Kathuria et al., *Multidrug-Resistant Candida auris Misidentified as Candida haemulonii: Characterization by Matrix-Assisted Laser Desorption Ionization—Time of Flight Mass Spectrometry and DNA Sequencing and Its Antifungal Suscepti-bility Profile Variability by Vitek 2, CLSI Broth Microdilution, and Etest Method*, 53 Journal of Microbiology 1823-1830 (June 2015), available at jcm.asm.org/content/53/6/1823.full.pdf+html. Thus, the QAC-containing medium alone may not entirely resolve the misidentification problems of the prior art, though research is ongoing.

After 48 hours of incubation at 38.5° C., however, *C. haemulonii* shows an increased sensitivity to cetylpyridinium chloride relative to *C. auris* (the opposite is found for *C. albicans*). Thus, *C. auris* can be distinguished from *C. haemulonii*. It should be noted that *C. auris*, unlike many other yeasts, is known to be able to grow at high temperatures (42° C. and above) but 38.5° C. is a temperature that still fully supports the growth of all tested yeast strains if untreated with cetylpyridinium chloride. Thus, the positive selection medium is based on the relative cetylpyridinium chloride resistance of *C. auris* at elevated temperatures.

Figure 3:
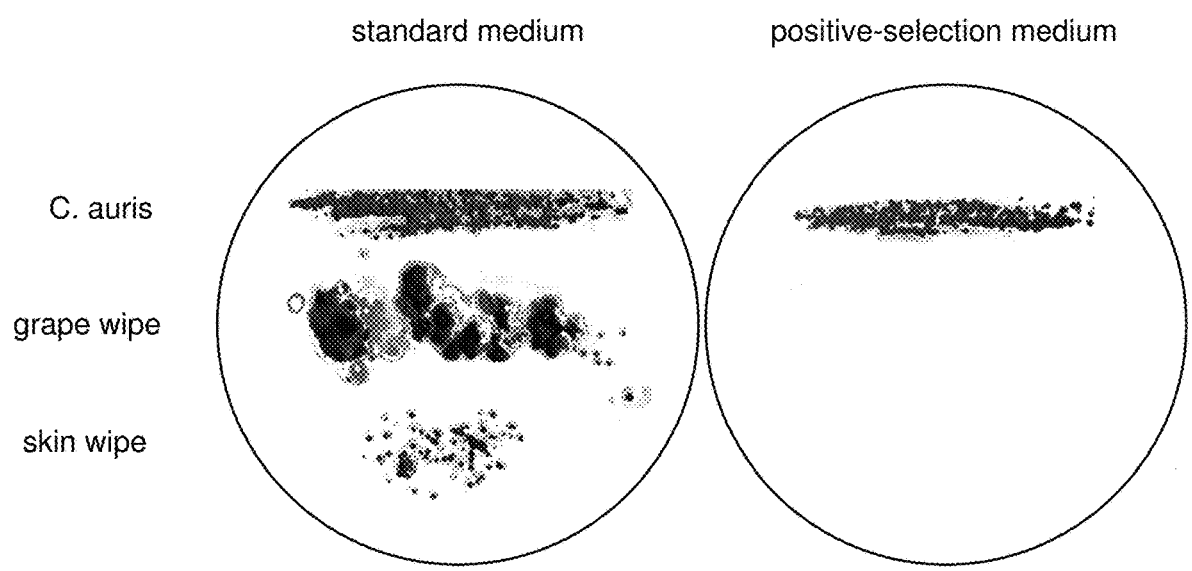
Figure 5A:
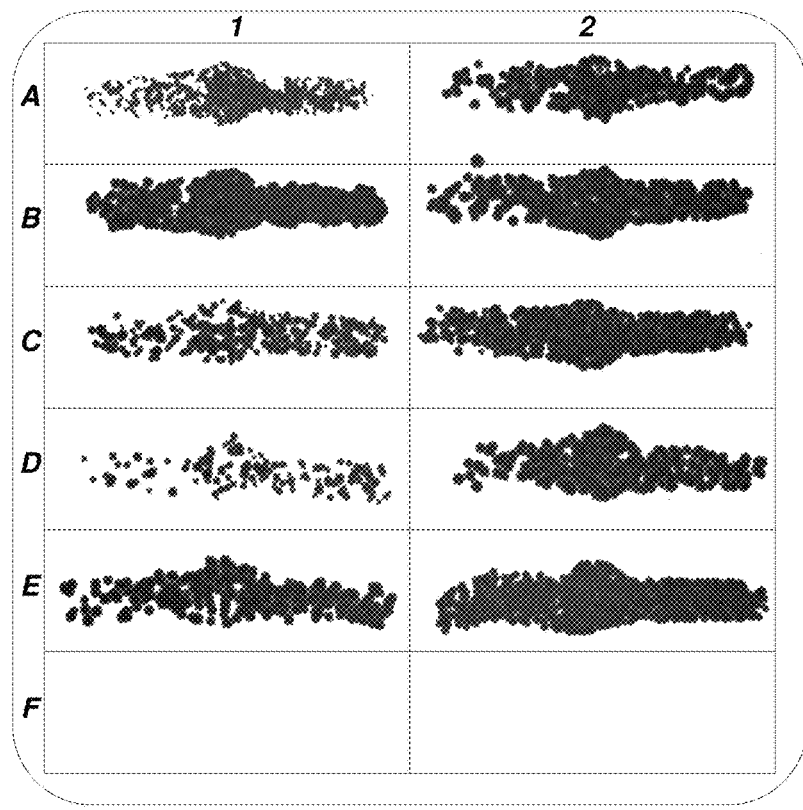
Figure 5B:
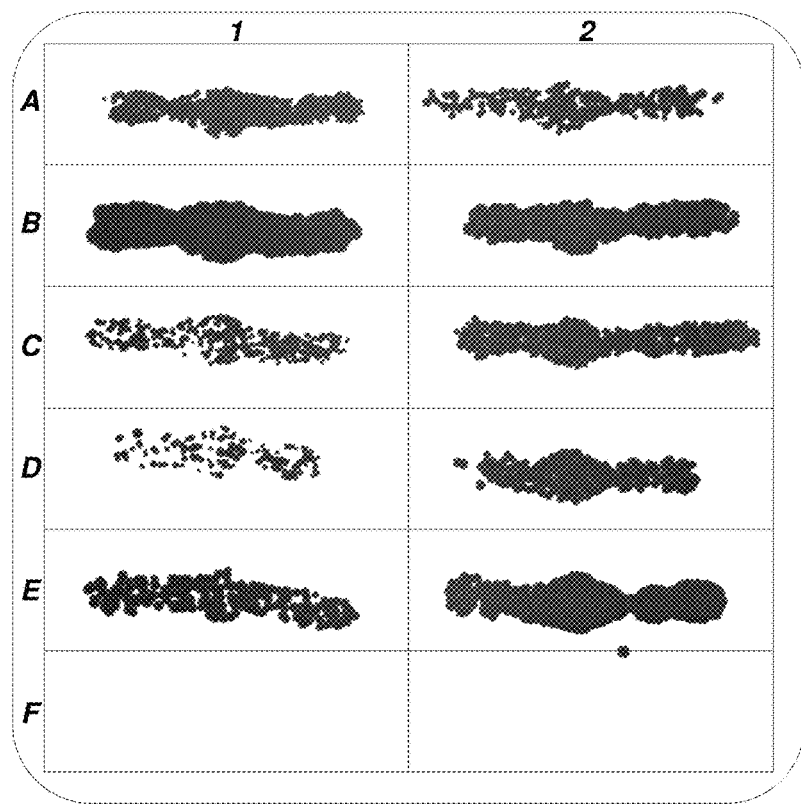
Figure 6:
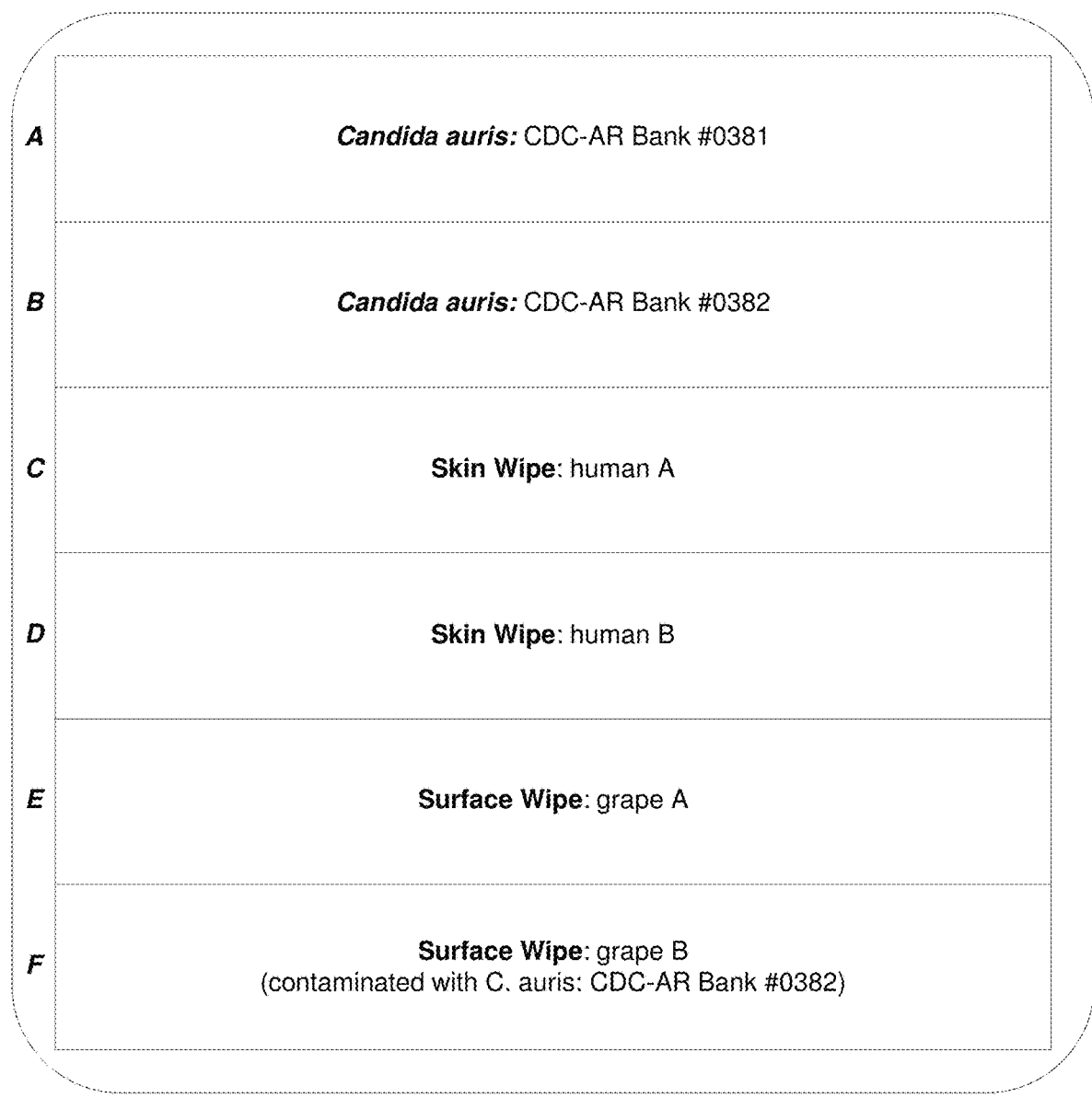
FIG. 6 depicts the plating scheme for the assays depicted in FIGS. 7A-7C.
Figure 7A:
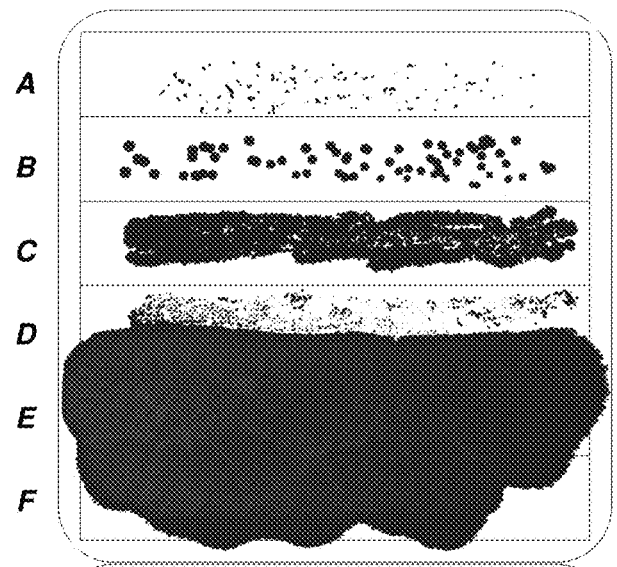
FIGS. 7A-7C depict plate assays for a variety of environmental samples using nonselective standard media (a yeast-extract-peptone-dextrose-based medium (YPD) and a brain-heart-infusion-based medium (BHI)) and a QAC-based positive-selection medium configured to support old *C. auris* cells.
Figure 7B:
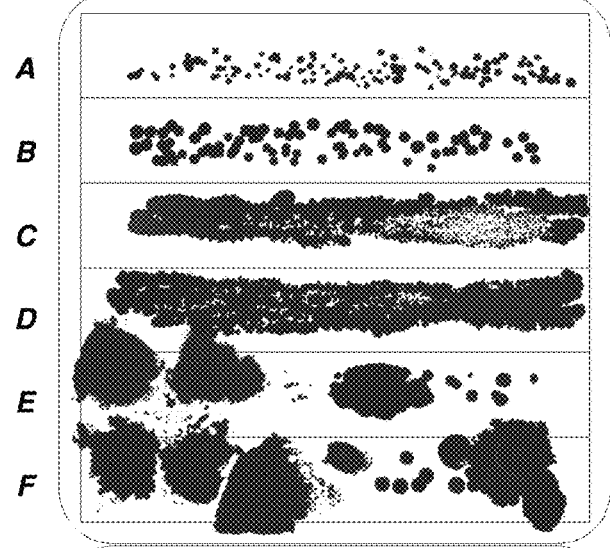
Figure 7C:
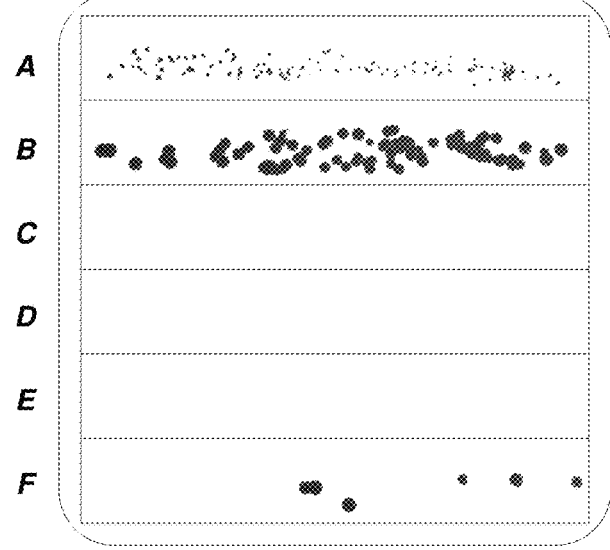
Figure 9A:
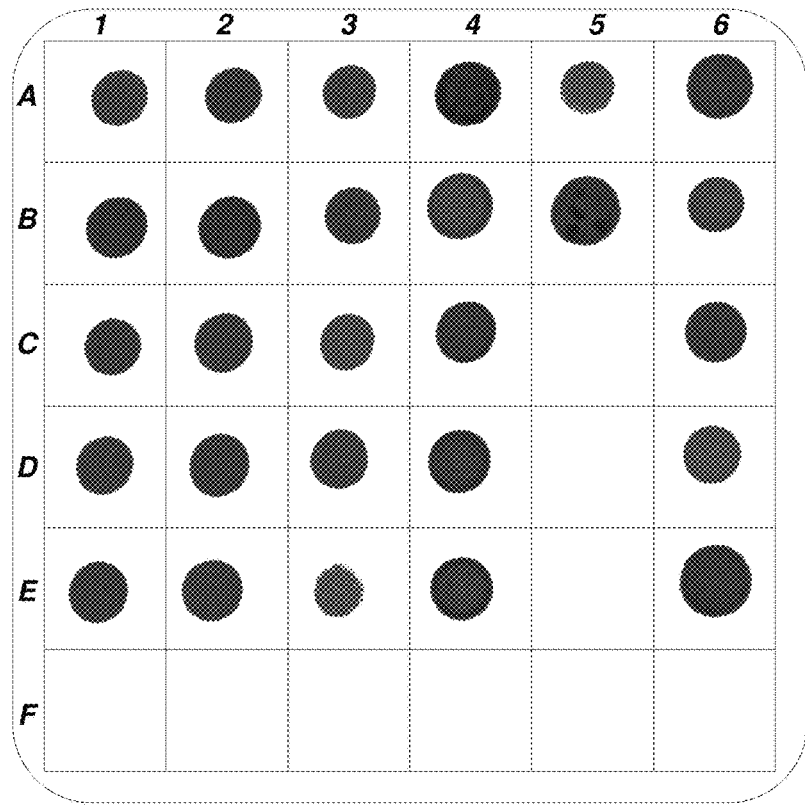
FIGS. 9A-10B depict plate assays for a variety of organisms using a QAC-free control medium and a QAC-based positive-selection medium configured to support old *C. auris* cells.
Figure 9B:
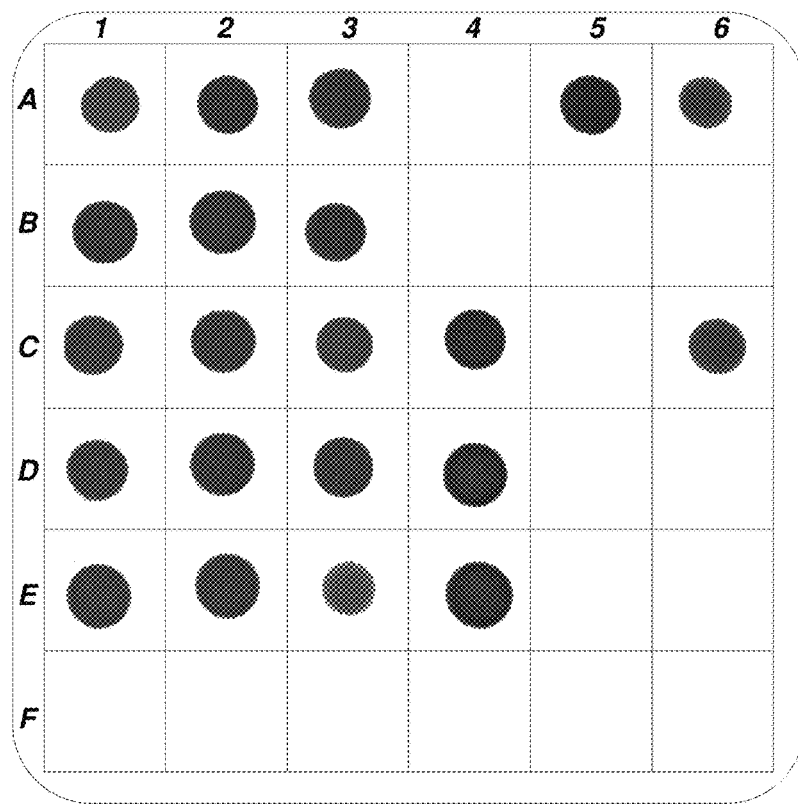
Figure 10A:
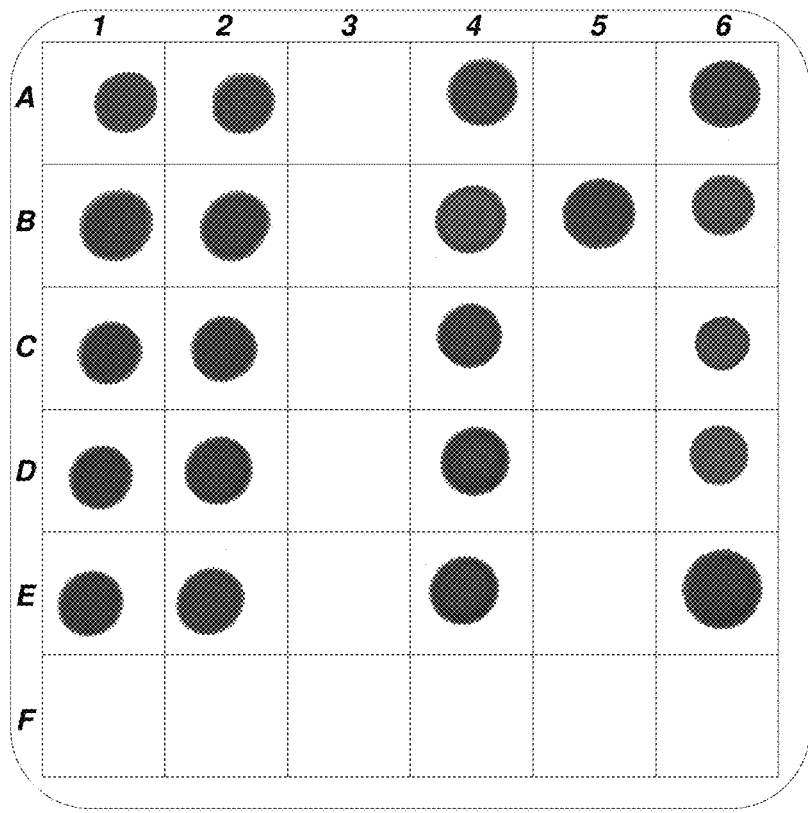
Figure 10B:
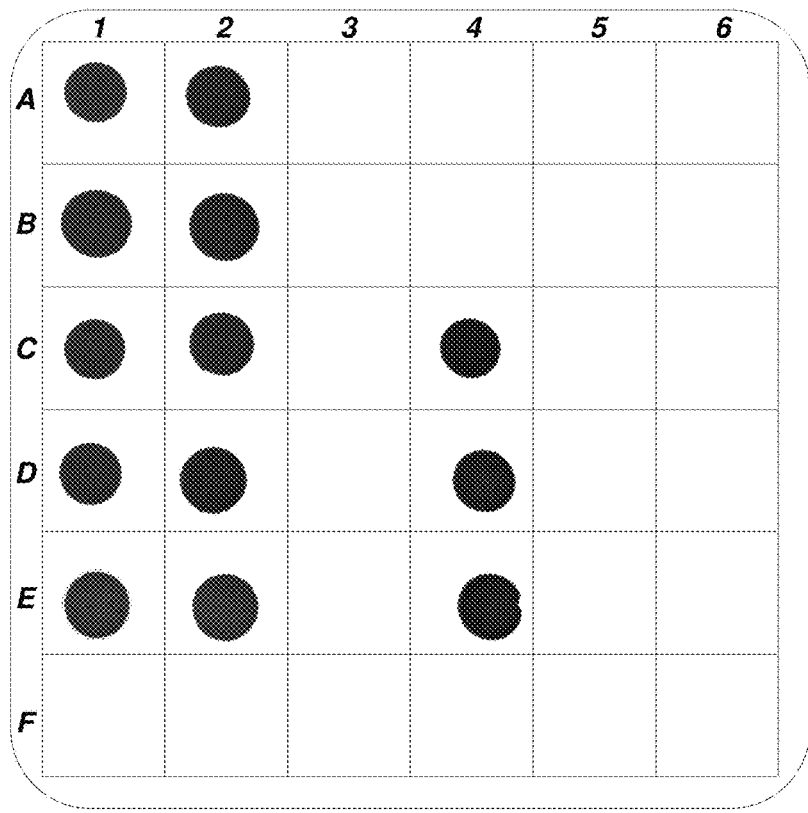

FIG. 3 illustrates the difference in response between cell-suspension samples cultured on a standard medium (left plate) and samples cultured on an exemplary QAC-containing positive-selection medium according to the invention (right plate). *C. auris* colonies (top culture on both plates) are the only visibly present culture on the QAC-containing medium. The middle sample (a wipe taken with a sterile cotton swab from the surface of an unwashed grape) and the bottom sample (human-skin wipe) present growing colonies on the standard medium but not on the QAC-containing medium.

A recipe for an exemplary positive-selection medium is as follows: Mix per one liter of deionized water (all % in weight/volume, subject to normal laboratory uncertainty): (1) a solidifying agent if procedure done on plates: 2% agar; (2) a sugar: 4% dextrose (autoclave separately, add after autoclaving); (3) a supplement mix: 0.7% Yeast Nitrogen Base with ammonium sulfate (commercial mix, autoclave separately, add after autoclaving); and (4) a Quaternary Ammonium Compound (all stocks dissolved at 2% in 91% isopropanol, add after autoclaving): cetylpyridinium chloride=8.5 ml or benzalkonium chloride=13 ml or tetradecyltrimethylammonium bromide=13 ml. It is possible to use other supplements such as peptone but there are differences, e.g. yeast extract is not recommended. As shown below, the nature of the supplement may critically modulate QAC sensitivity in a species-specific manner to improve positive selection of *C. auris*. Variations in ingredients may also improve the initial selection of *C. auris* within samples that may contain a multitude of other microorganisms which need to be suppressed. For example, the following adaptations (alone or in combinations) may be implemented: (1) Add extra isopropanol (or dissolve the QAC at a lower concentration in isopropanol). Could go up to 3%. *C. auris* of approximately 1-12 days of culture age is very resistant to isopropanol but many other organisms are not. This approach may not be appropriate if it is possible that older *C. auris* is present because *C. auris* of about 12-days of culture age or older is less resistant to isopropanol than is younger *C. auris*. (2) Lower the amount of Yeast Nitrogen Base. Can go down to 0.14% which makes the medium less rich. This is no problem for *C. auris* but fewer organisms will grow. (3) Add 25 µg/ml chloramphenicol (stock: 50 mg/ml in ethanol, a standard method to suppress bacteria). Samples are placed on solid media by, for example, streaking or dropping suspension. The inoculated medium is incubated at approximately 38.5° C. and evaluated after as early as 36 hours, preferably after about 48 to 60 hours.

Two-Step Positive-Selection System: In circumstances potentially involving old *C. auris* cells (e.g., 12 days old or older) or certain other yeasts such as *Candida lusitaniae* and certain strains of *Saccharomyces cerevisiae*, it is preferable to use a two-step process at 37° C. The first step involves a first positive-selection medium (the "Step-1 Medium") that has been modified to the allow uninhibited growth of colonies from old *C. auris* cells which may be of concern in the surveillance of surface contamination (e. g. in hospitals). Type and concentration of QAC are selected to minimize impact on old *C. auris* cells, isopropanol is not used as a solvent, and the incubation temperature is 37° C. This Step-1 Medium may not, however, uniquely select *C. auris*. For example, *C. lusitaniae* and certain strains of *S. cerevisiae* may grow on or in such a medium, even when incubated at an elevated temperature (e.g., 37° C.). The second step involves a second positive-selection medium (the "Step-2 Medium") and cells cultured with the first medium. Because the cells for the second step come from the colonies formed in the first step, the risk of failing to detect *C. auris* because of the age of the cells is not present. The Step-2 Medium is formulated to suppress growth of *C. lusitaniae* and *S. cerevisiae* when incubated at an elevated temperature (e.g., 37° C.). Thus, the Step-2 Medium is designed to positively uniquely select *C. auris* without concern for the age of the cells. Together, the Step-1 Medium and the Step-2 Medium positively select for *C. auris* without significant loss of old *C. auris* cells and without significant risk of misidentification of another yeast as *C. auris*. Other organisms are also efficiently suppressed (as outlined below).

A Step-1 Medium includes: (1) a higher dextrose content (relative to standard media) to inhibit bacterial growth, (2) an antibiotic to inhibit bacterial growth, (3) a nutritionally poor (with no amino acids) and defined supplement mixture to inhibit growth of bacteria, yeast, and molds with complex growth requirements, and (4) a QAC or a combination of more than one QAC to generally suppress the growth of organisms other than *C. auris*.

An exemplary recipe for a solid Step-1 Medium is as follows: Mix per one liter of deionized water: (1) 20 g agar; (2) 60 g dextrose (add from 200 g/l stock solution after autoclaving); (3) 25 mg chloramphenicol (add from a 50 mg/ml stock in ethanol after autoclaving); (4) 6.7 g Yeast Nitrogen Base without amino acids and with ammonium sulfate (YNB) (add from 67 g/l stock in water after autoclaving); (5) 70 mg benzalkonium chloride (add from a 10 mg/ml stock in water after autoclaving); and (6) 80 mg tetradecyltrimethylammonium bromide (add from a 20 mg/ml stock in water after autoclaving).

As shown in FIGS. 4, 5A, and 5B, an exemplary Step-1 Medium supports the growth of even old *C. auris* cells. The plating scheme for this test is shown in FIG. 4. Suspensions of ten different *C. auris* strains, CDC-AR Bank #0381-#390, were made in sterile deionized water, kept for 25 days at room temperature, and diluted. Drops (10 μl) of the diluted solutions were streaked on a control medium and a Step-1 Medium plate. The inoculated control medium, a standard Sabouraud-dextrose medium, was incubated at 30° C. for 48 hours. (The control conditions are known to be favorable to the growth of *C. auris*.) The inoculated Step-1 Medium was incubated at 37° C. for 72 hours. The number of *C. auris* colonies formed on the Step-1 Medium (FIG. 5B) is approximately the same as the number formed on the control medium (FIG. 5A). While the size of the colonies may differ between the control and the Step-1 Medium, having the same number of colonies indicates that the Step-1 Medium supports old *C. auris* cells to the same extent as the control.

As shown in FIGS. 6, 7A, 7B, and 7C, an exemplary Step-1 Medium inhibits the growth of commonly occurring organisms while supporting the growth of *C. auris*. Samples of *C. auris* (pure), human skin wipes, and grape surface wipes were streaked on three different media—two control media and Step-1 Medium. One of the grape wipes (grape B) was from a grape purposefully contaminated with *C. auris*. The media were incubated at either 30° C. or 37° C. The results are depicted in FIGS. 7A-7C. The plating scheme for this test is shown in FIG. 6. FIG. 7A depicts an assay using yeast extract, peptone, and dextrose (YPD) medium. The YPD medium supports the growth of a wide variety of organisms while favoring yeasts and molds due to dextrose content. The inoculated YPD medium was incubated at 30° C. for 48 hours. Colonies grew for each sample, but the *C. auris* colonies from the grape-B wipe (plate row F in the figure) are not distinguishable from other organisms due to the intense growth of other organisms (mold). FIG. 7B depicts an assay using brain heart infusion (BHI) medium. The BHI medium supports the growth of a wide variety of organisms while favoring bacteria. The inoculated BHI medium was incubated at 37° C. for 72 hours. Colonies grew for each sample. Some of the *C. auris* from the grape-B wipe (plate row F in the figure) are seen to grow among other organisms (bacteria and molds, the latter growing slower as in 7A due to less favorable conditions). FIG. 7C depicts an assay using Step-1 Medium. Here, only *C. auris* colonies grew (plate rows A, B, and F in the figure) and can thus be clearly identified as the only growing species in a mixed sample of various organisms (compare row F in FIGS. 7A-7C).

Two other tests of Step-1 Medium are depicted in FIGS. 8-10B. Suspensions of various organisms were made from samples provided by the CDC, ATCC (American Type Culture Collection), and DSMZ (German Collection of Microorganisms and Cell Cultures). Drops (10 μl) of the solutions containing approximately $2\times10^5$ cells (calculated) were placed on two media: a control medium plate (a Step-1 Medium without a QAC) and a Step-1 Medium plate. The plating scheme is shown in FIG. 8. One inoculated control medium plate and one inoculated Step-1 Medium plate were incubated at 30° C. for 48 hours (FIGS. 9A-9B). A second inoculated control medium plate and a second inoculated Step-1 Medium plate were incubated at 37° C. for 48 hours (FIGS. 10A-10B). The difference between FIGS. 9A and 9B shows that the Step-1 Medium suppressed the growth of four organisms at 30° C.: *K. ohmeri*, *C. krusei* (CDC AR #0397), *C. krusei* (ATCC14243), and *C. glabrata*. See plate cells (A, 4), (B,4), (B,5), and (B,6), respectively (denoted as (row, column)). The difference between FIGS. 10A and 10B shows that the Step-1 Medium suppressed the growth of four additional organisms at 37° C.: *C. albicans, C. famata, C. parapsilosis, C. tropicalis*. See plate cells (A,6), (C,6), (D,6), and (E,6) respectively. (The higher incubation temperature suppressed the growth of *C. duobushaemulonii* (CDC AR #0391), *C. duobushaemulonii* (CDC AR #0392), *C. haemulonii* (CDC AR #0393), *C. duobushaemulonii* (CDC AR #0394), and *C. haemulonii* (CDC AR #0395). See plate cells (A,3), (B,3), (C,3), (D,3), and (E,3) respectively. The surviving organisms were all ten strains of *C. auris* (plate columns 1 and 2), *C. lusitaniae* (plate cell (C,4)), and two strains of *S. cerevisiae* (plate cells (D,4) and (E,4)).

Step-2 Medium includes: (1) a higher dextrose content (relative to standard media) to inhibit bacterial growth, (2) an antibiotic to inhibit bacterial growth, (3) a nutritionally rich (with amino acids) and complex supplement mixture to modulate the *C. auris* QAC sensitivity vis-à-vis YNB, and (4) a QAC or a combination of more the one QAC to suppress the growth of organisms other than *C. auris* (including by suppressing *C. lusitaniae* and *S. cerevisiae*).

An exemplary recipe for solid Step-2 Medium is as follows: Mix per one liter of deionized water: (1) 20 g agar; (2) 60 g dextrose (add from 200 g/l stock solution after autoclaving); (3) 25 mg chloramphenicol (add from a 50 mg/ml stock in ethanol after autoclaving); (4) 10 g peptone (meat); and (5) 130 mg benzalkonium chloride (add from a 10 mg/ml stock in water after autoclaving).

Figure 11A:
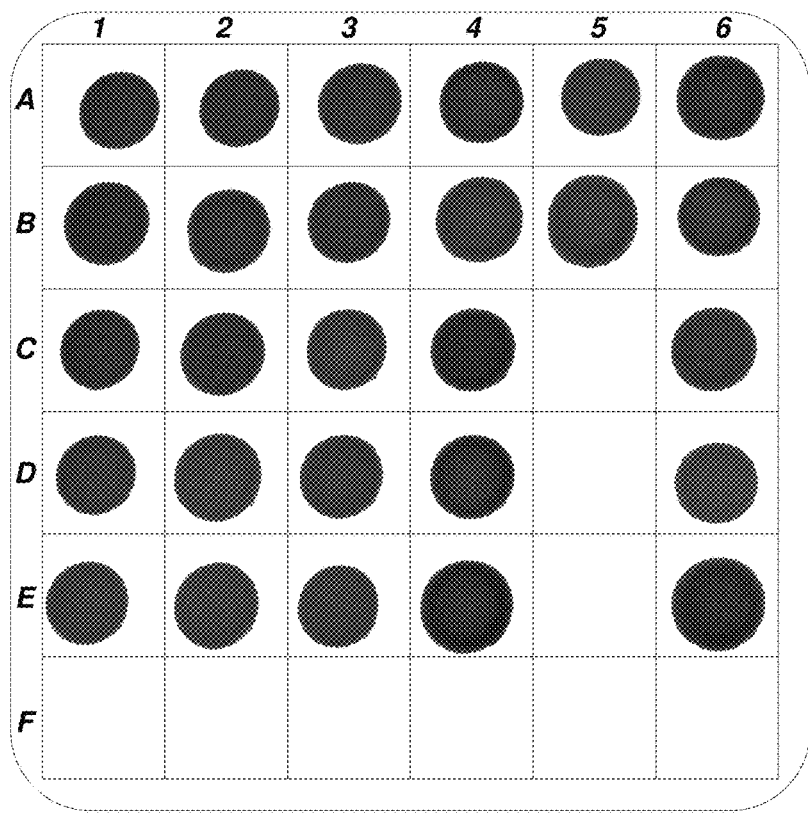
FIGS. 11A-12B depict plate assays for a variety of organisms using a QAC-free control medium and a QAC-based positive-selection medium.
Figure 11B:
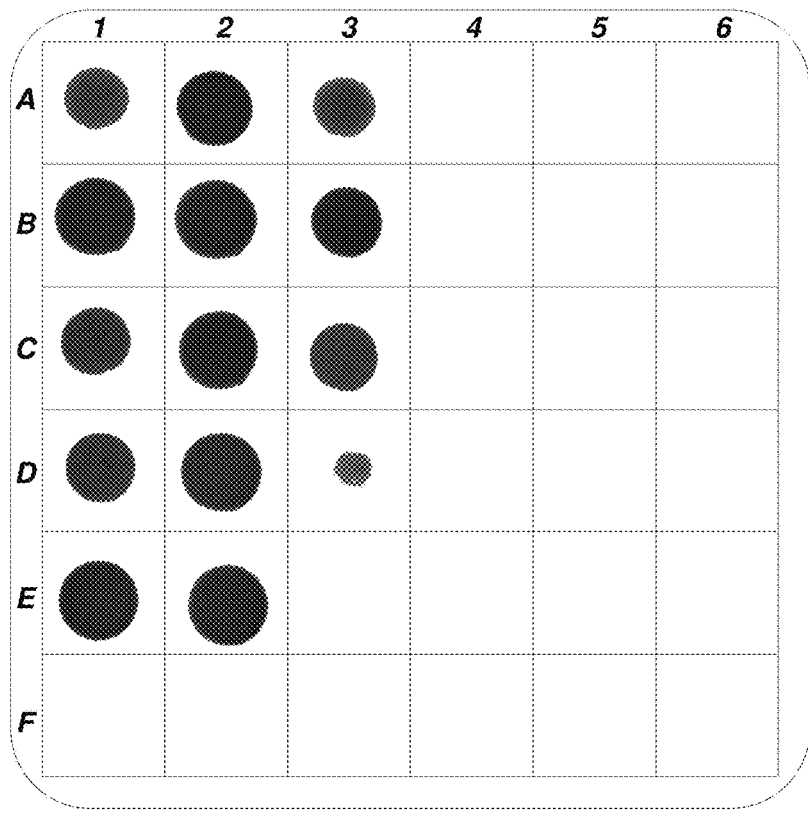
Figure 12A:
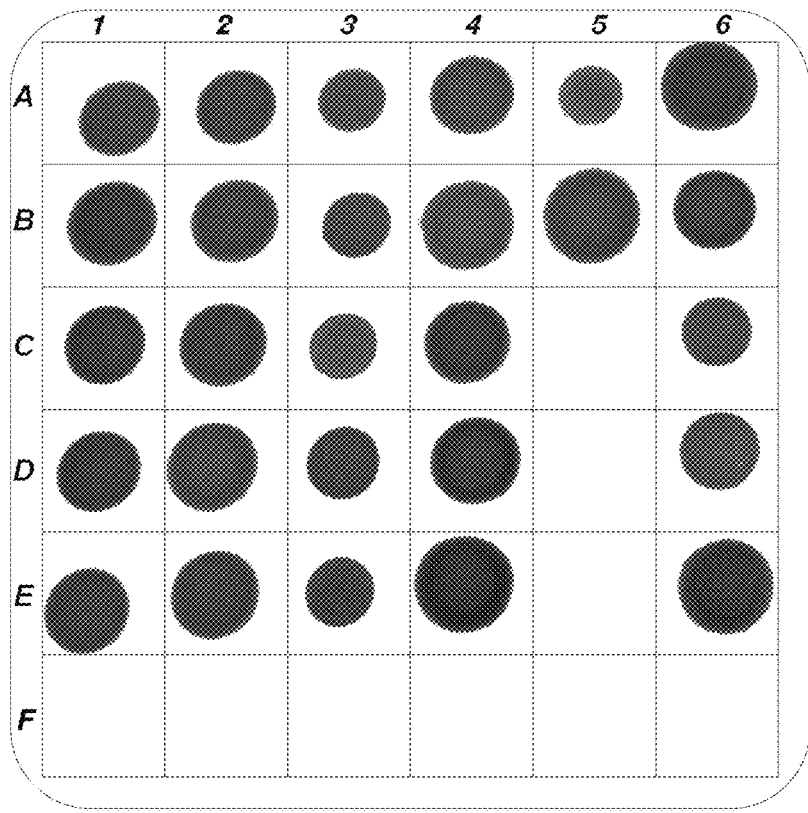
Figure 12B:
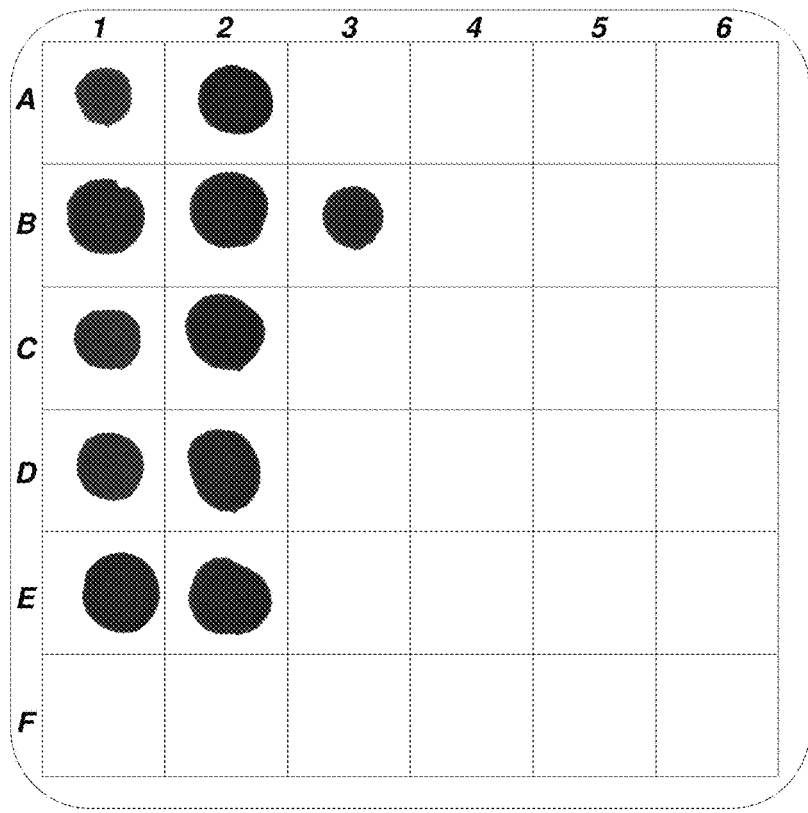
Figure 14A:
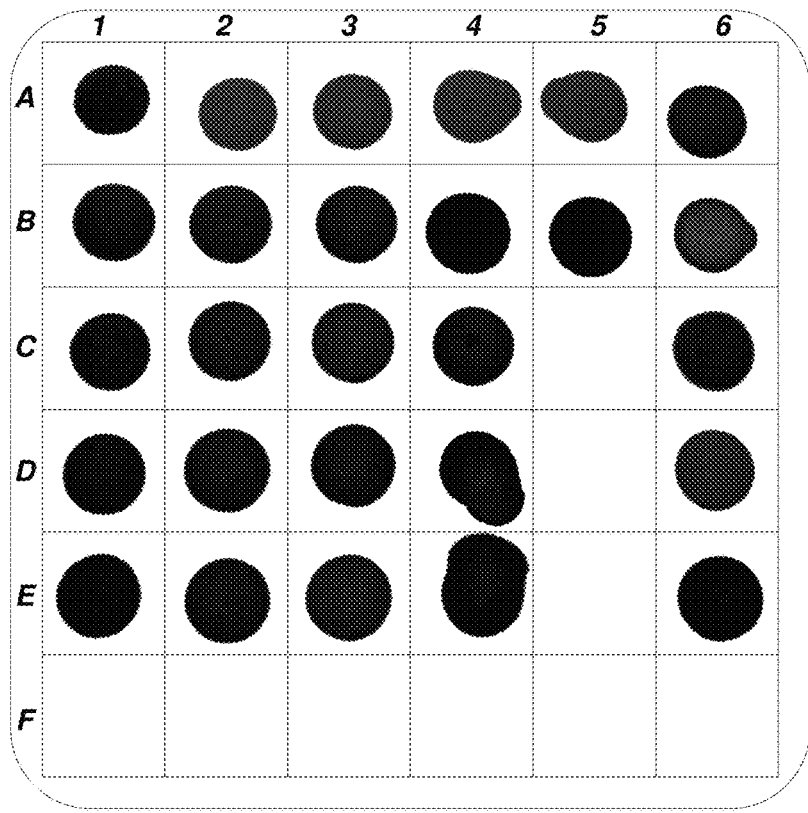
FIGS. 14A-14B depict plate assays for a variety of organisms using a tBHP-free, tryptone-based, nonselective, control culture medium (FIG. 14A) and a negative-selection culture medium containing tert-butyl-hydroperoxide (FIG. 14B).
Figure 14B:
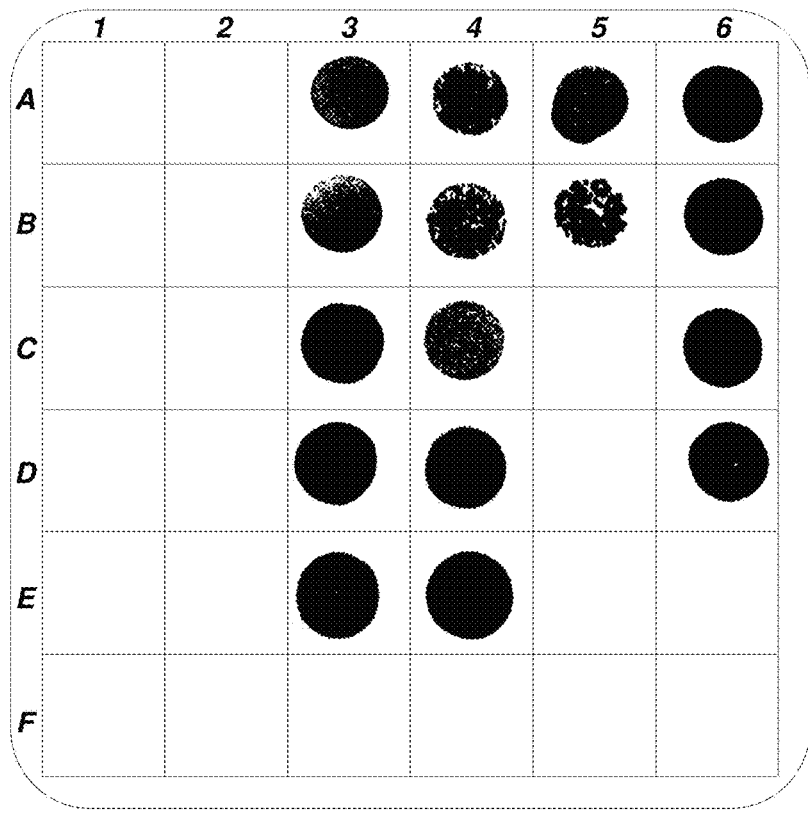

Tests of Step-2 Medium are depicted in FIGS. 8, 11A-12B. Suspensions of various organisms were made from samples provided by the CDC, ATCC, and DSMZ. Drops (10 µl) of the suspensions containing approximately $2\times10^5$ cells (calculated) were placed on plates of two media: control medium (Step-2 Medium without a QAC) and Step-2 Medium. The plating scheme is shown in FIG. 8. One inoculated control medium plate and one inoculated Step-2 Medium plate were incubated at 30° C. for 48 hours (FIGS. 11A-11B). A second inoculated control medium and a second inoculated Step-2 Medium were incubated at 37° C. for 48 hours (FIGS. 12A-12B). The difference between FIGS. 11A and 11B shows that at 30° C. the Step-2 Medium suppressed the growth of organisms other than *C. auris* (plate columns 1 and 2) and *C. duobushaemulonii* (CDC AR #0391), *C. duobushaemulonii* (CDC AR #0392), *C. haemulonii* (CDC AR #0393), and *C. duobushaemulonii* (CDC AR #0394) (plate cells (A,3), (B,3), (C,3), and (D,3)). The difference between FIGS. 12A and 12B shows that at 37° C. the Step-2 Medium suppressed the growth of organisms other than *C. auris* (plate columns 1 and 2) and *C. duobushaemulonii* (CDC AR #0392) (plate cell (B,3)).

There are two points of note from the tests depicted in FIGS. 8-12B: (1) The Step-2 Medium suppressed the growth of the non-*C. auris* survivors of the Step-1 Medium at 37° C. incubation: *C. lusitaniae* (plate cell (C,4)) and *S. cerevisiae* (plate cells (D,4) and (E,4)). (2) The non-*C. auris* survivor of the Step-2 Medium at 37° C. incubation, *C. duobushaemulonii* (CDC AR #0392) (plate cell (B,3)), did not survive the Step-1 Medium at 37° C. incubation. This indicates that the Step-1 Medium and Step-2 Medium can be used in concert to uniquely identify *C. auris*. Step-1 Medium with incubation at 37° C. would select a candidate set that includes *C. auris*, *C. lusitaniae* (plate cell (C,4)), and *S. cerevisiae*, but not the other organisms. A sample taken from this candidate set will survive a 37° C. incubation on a Step-2 Medium only if the sample is *C. auris*.

Negative Selection System: *C. auris* has a relatively high sensitivity to the oxidizing agent tert-butyl-hydroperoxide ("tBHP"). Hence, tBHP can be used as the basis of a negative-selection medium.

FIGS. 13A-13B illustrate *C. auris*'s relative sensitivity to tBHP. FIG. 13A depicts a plate with a tBHP-containing culture medium that includes seven different yeasts (*Candida albicans, Candida glabrata, Candida krusei, Candida auris, Candida haemulonii, Candida famata*, and *Saccharomyces cerevisiae*) at five different calculated cell counts (62, 625, 6,250, 62,500, with the uncertainty inherent in the calculation). The yeast-containing plate was incubated at 30° C. The plating scheme is illustrated in FIG. 1. The culture medium comprised a Sabouraud dextrose medium with tBHP (added after autoclaving the other media ingredients from a 70% solution in water). Whereas a resuspension of cells picked from a colony will always enhance the sensitivity of this (and related) assays, it is possible to streak cells without any dilution directly from a colony if the plate is evaluated early (after approximately 24 hours, some regrowth will occur later), as depicted in FIG. 13B.

FIGS. 14A-14B further illustrate *C. auris*'s relative sensitivity to tBHP. The plating scheme for this test is shown in FIG. 8. Suspensions of various organisms were made from samples provided by the CDC, ATCC (American Type Culture Collection), and DSMZ (German Collection of Microorganisms and Cell Cultures). Drops (10 μl) of the solutions containing approximately $2\times10^5$ cells (calculated) were placed on two media: a tBHP-free control medium plate and a tBHP-based negative-selection medium plate. The plating scheme for this test is shown in FIG. 8. The inoculated media were incubated at 30° C. for 24 hours. The standard medium (FIG. 14A) supported the growth of all the organisms. The negative-selection medium (FIG. 14B) suppressed the growth of all ten *C. auris* strains (plate columns 1 and 2), as well as *C. tropicalis* (plate cell (E,6)).

In use of a negative-selection medium, samples are added to the medium by, for example, streaking or dropping suspension. The inoculated medium is incubated at approximately 30° C. and evaluated after 22-26 hours. The accuracy and robustness of such an assay may be improved by first culturing the samples on a non-selective medium, such as a standard Sabouraud-dextrose medium, and then taking samples from the cultures and applying to the negative-selection medium. For example, samples may be placed on a standard medium, incubated at 30° C. for 24-48 hours, and then samples of the cultures placed on the negative-selection medium and incubated at 30° C. for about 24 hours. Lack of growth on the negative-selection medium indicates the samples are *C. auris* (or *C. tropicalis*, if that yeast is not first eliminated by, e.g., use of a positive-selection medium).

A recipe for an exemplary negative-selection medium is as follows: Mix per one liter of deionized water (all % in weight/volume, subject to normal laboratory uncertainty): (1) a solidifying agent if procedure done on plates: 2% agar; (2) a sugar: 4% dextrose (autoclave separately, add after autoclaving); (3) a supplement mix: 1% peptone; and (4) the oxidizing agent tert-butyl-hydroperoxide (tBHP): 350 μl (from a 70% solution in water, add after autoclaving).

Another recipe for an exemplary solid negative-selection medium is as follows: Mix per one liter of deionized water: (1) 20 g agar; (2) 60 g dextrose (add from 200 g/l stock solution after autoclaving); (3) 25 mg chloramphenicol (add from a 50 mg/ml stock in ethanol after autoclaving); (4) 20 g tryptone; and (5) 300 μl tert-butyl-hydroperoxide (add from 70% solution in water after autoclaving).

As depicted in the exemplary flow charts of FIGS. 15-17, use of the *C. auris* positive-selection and negative-selection media can be combined in various ways to increase the accuracy of *C. auris* identification (i.e., to lower the number of false positives and false negatives). FIG. 15 illustrates an assay using a defined-supplement QAC-based positive-selection medium and a tBHP-based negative-selection medium. A sample is collected from the environment of interest 1501 and is used to inoculate the defined-supplement QAC-based positive-selection medium 1502 (e.g., the Step-1 Medium described above). The inoculated medium is incubated at an elevated temperature (~37° C.) for about 72 hours 1503. The medium is then examined 1504: if no growing cultures are present, then one can conclude (within a margin of uncertainty) that the sample does not include *C. auris* 1505, if cultures have grown, then a candidate sample from the culture is collected 1506 for further analysis using a tBHP-based negative-selection medium. The candidate sample is used to inoculate a standard non-selective medium (e.g., a Sabouraud-dextrose medium) 1507, which is then incubated at standard temperature (~30° C.) for about 36-48 hours 1508. A candidate sample is then collected from the resulting cultures 1509 and used to inoculate a tBHP-based negative-selection medium 1510. The inoculated negative-selection medium is incubated at a standard yeast-incubation temperature (~30° C.) for 22-26 hours 1511. The medium is then examined 1512: if no cultures have grown, then one can conclude (within a margin of uncertainty) that the sample does include *C. auris* 1514, if cultures have grown, then one can conclude (within a margin of uncertainty) that the sample does not include *C. auris* 1513.

Figure 16:
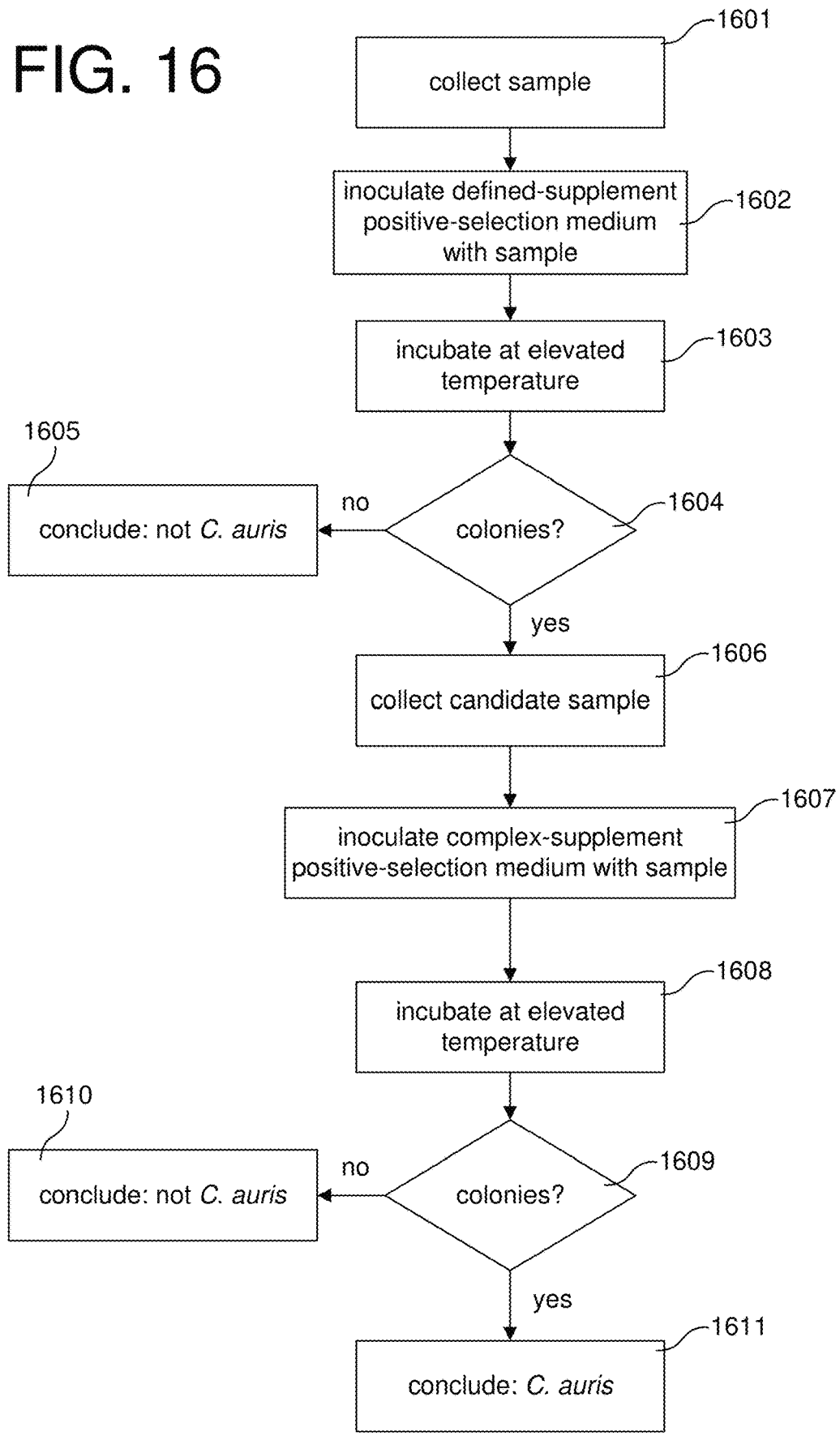

An assay using a defined-supplement QAC-based positive-selection medium and a complex-supplement QAC-based positive-selection medium is depicted in FIG. 16. As with the previous flows: a sample is collected from the environment 1601 and is used to inoculate a defined-supplement QAC-based positive-selection medium 1602 (e.g., the Step-1 Medium described above), the inoculated medium is incubated at an elevated temperature 1603, and then examined for the presence of growing cultures 1604. If there are no cultures present, one can conclude the sample does not include *C. auris* 1605. Otherwise, a candidate sample is collected from the culture 1606 and used to inoculate a complex-supplement QAC-based positive-selection medium 1607 (e.g., the Step-2 Medium described above), which is then incubated at an elevated temperature (~37° C.) for about 36-48 hours 1608. The medium is then examined 1609: if no cultures have grown, then one can conclude (within a margin of uncertainty) that the sample does not include *C. auris* 1610, if cultures have grown, then one can conclude (within a margin of uncertainty) that the sample does include *C. auris* 1611.

Figure 17:
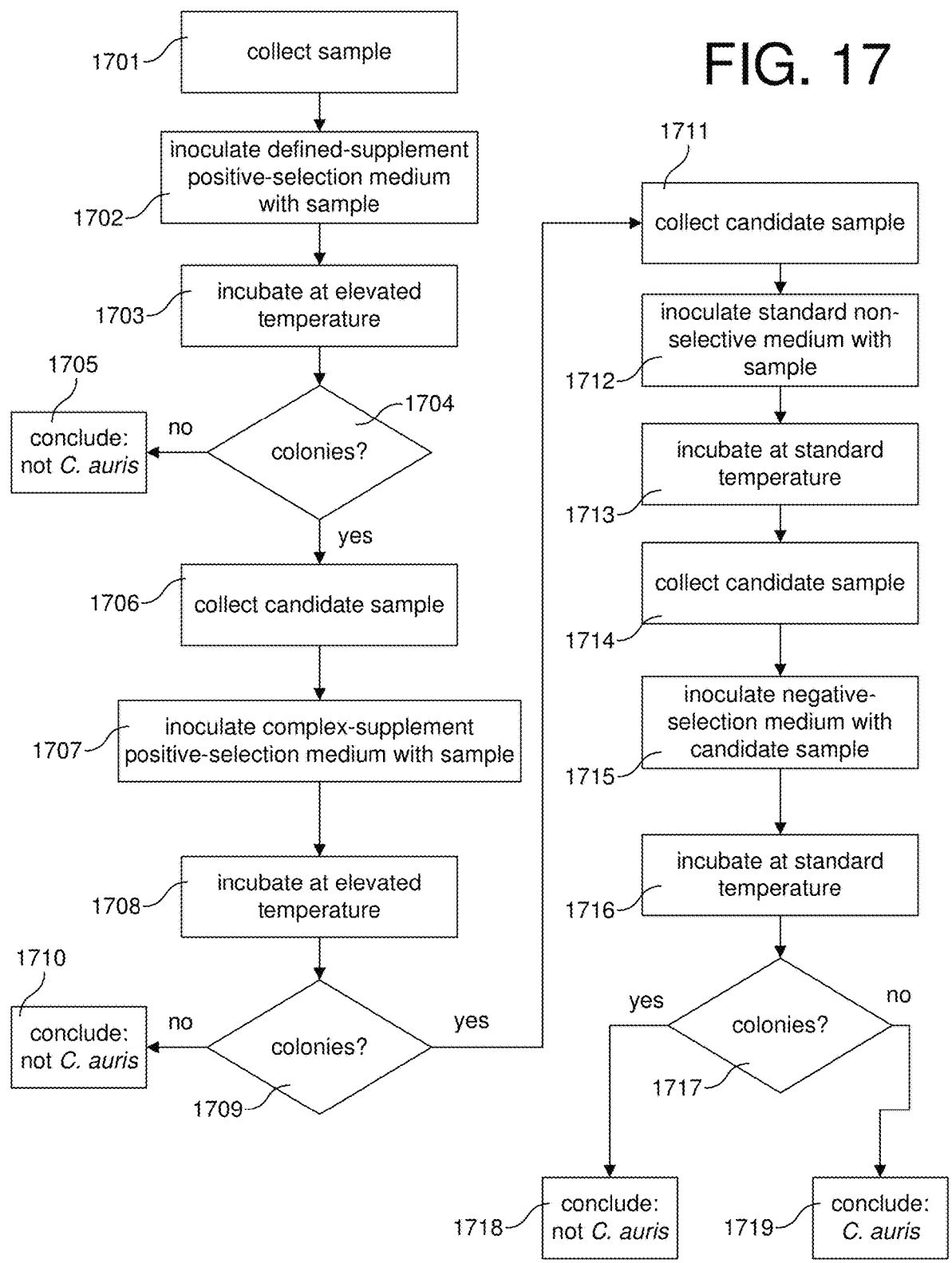

The assay illustrated in FIG. 17 adds a negative-selection component to the assay of FIG. 16. Steps 1701 through 1709 of FIG. 17 are identical to steps 1601 through 1609 of FIG. 16 respectively, except that if incubation of the complex-supplement QAC-based positive-selection medium 1708 yields growing cultures 1709, then a candidate sample is collected from the complex-supplement QAC-based positive-selection medium 1711 and subject to a negative-selection assay. The candidate sample is used to inoculate a standard non-selective medium (e.g., a Sabouraud-dextrose medium) 1712, which is then incubated at standard temperature (~30° C.) for about 24-48 hours 1713. A candidate sample is then collected from the resulting cultures on the non-selective medium 1714 and used to inoculate a tBHP-based negative-selection medium 1715. The inoculated negative-selection medium is incubated at a standard yeast-incubation temperature (~30° C.) for about 22-26 hours 1716. The medium is then examined 1717: if no growing cultures are present, then one can conclude (within a margin of uncertainty) that the sample does include *C. auris* 1719, if growing cultures are present, then one can conclude (within a margin of uncertainty) that the sample does not include *C. auris* 1718.

Figure 15:
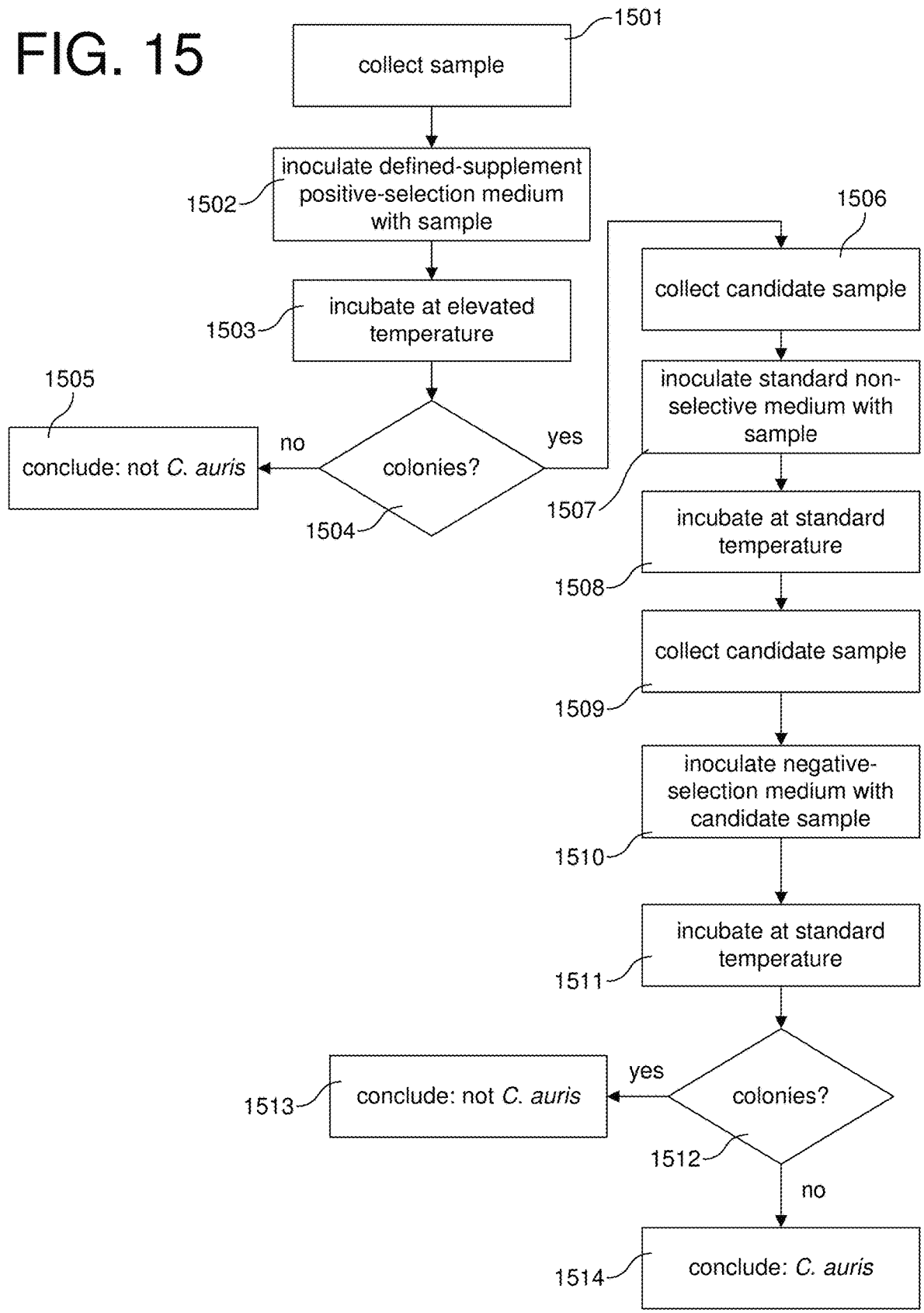
FIGS. 15-18 depict flow charts for exemplary assays to detect *C. auris*.

While the steps of the exemplary assays depicted in FIGS. 15-17 are illustrated as proceeding sequentially, certain steps may also proceed in parallel. For example, the flow depicted in FIG. 18 includes three assays performed in parallel. In this exemplary assay, a common sample is used to inoculate three different media: a defined-supplement QAC-based positive-selection medium 1803, a complex-supplement QAC-based positive-selection medium 1813, and a tBHP-based negative-selection medium 1823. Each inoculated medium is incubated: the defined-supplement QAC-based positive-selection medium at an elevated temperature (~37° C.) for about 72 hours 1805, the complex-supplement QAC-based positive-selection medium at an elevated temperature (~37° C.) for about 36-48 hours 1815, and the tBHP-based negative-selection medium at a standard yeast-incubation temperature (~30° C.) for 22-26 hours 1825. The incubated media are examined for cultures 1807, 1817, 1827. If cultures grew on the defined-supplement QAC-based positive-selection medium, then the assay is a positive indication of *C. auris* (*C. auris* present in the sample) 1811. Otherwise, it is a negative indication of *C. auris* (*C. auris* not present in the sample) 1809. If cultures grew on the complex-supplement QAC-based positive-selection medium, then the assay is a positive indication of *C. auris* (present in the sample) 1821. Otherwise, it is a negative indication of *C. auris* (not present in the sample) 1819. If cultures grew on the tBHP-based negative-selection medium, then the assay is a negative indication of *C. auris* (not present in the sample) 1831. Otherwise, it is a positive indication of *C. auris* (present in the sample) 1829. Three positive results suggest the presence of *C. auris* in the sample. Three negative results suggest the absence of *C. auris* in the sample. Mixed results call for further investigation. It should be noted that direct evaluation of an environmental sample may not be possible in this manner since only the defined-supplement QAC medium is specifically designed to prevent the growth of unwanted microorganisms, such as bacteria or molds. Thus, it may not be easy to identify yeast colonies among the background growth of other organisms on the other media. However, this approach is feasible if single candidate yeast colonies are to be tested that have been isolated previously by other methods.

Figure 18:
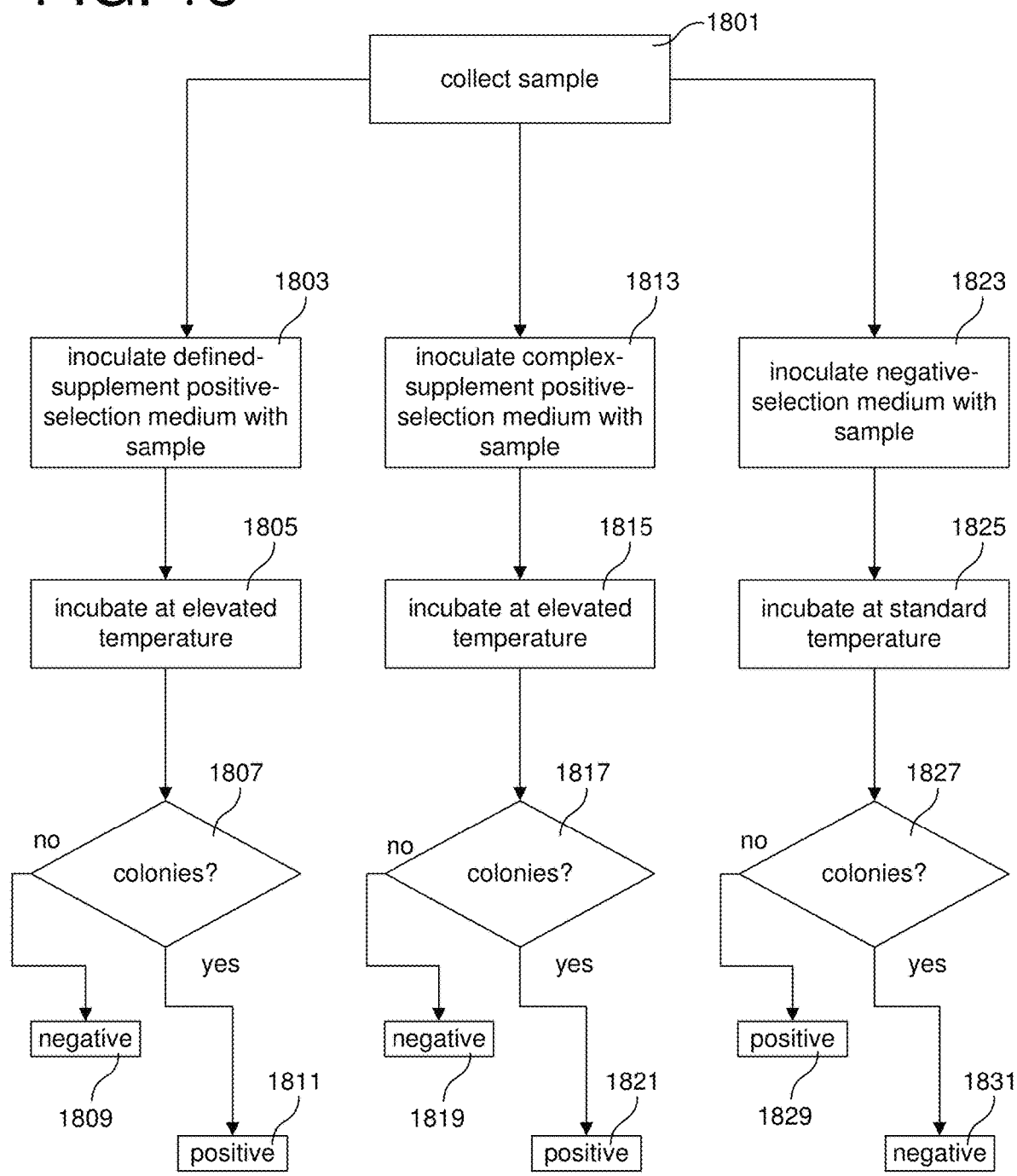

Another exemplary parallel assay would include a first step of inoculating and incubating a defined-supplement QAC-based positive-selection medium, as described above with reference to items 1801 to 1811 in FIG. 18. If the first step yields cultures (a positive indication of *C. auris*), those cultures are used to: (1) inoculate and incubate a complex-supplement positive-selection medium, as described above with reference to items 1813-1821 of FIG. 18, and, in parallel, (2) inoculate and incubate a tBHP-based negative-selection medium, as described above with reference to items 1823-1831 of FIG. 18 (perhaps with intervening culturing on a nonselective culture medium).

Exemplary Applications. The positive/negative selection systems may be most valuable in monitoring of patient/visitor/staff colonization or environmental contamination in a hospital environment and lends itself to large-scale testing. Such monitoring and, if needed, epidemiological investigation and source identification, is of particular importance for *C. auris* which shows a high propensity for patient-to-patient transmission. The positive/negative selection systems may be especially important in a healthcare setting in a less-developed country where sophisticated diagnostics are not readily available. Initial clues to the nature of the pathogen can thus be obtained, leading to more targeted testing. The positive/negative selection systems may be incorporated in automated diagnostic systems, such as VITEK, that use similar metabolic and growth criteria. This would aid accurate identification of *C. auris*.

While the foregoing description is directed to the preferred embodiments of the invention, other and further embodiments of the invention will be apparent to those skilled in the art and may be made without departing from the basic scope of the invention. And features described with reference to one embodiment may be combined with other embodiments, even if not explicitly stated above, without departing from the scope of the invention. The scope of the invention is defined by the claims which follow.

The invention claimed is:

1. A *Candida-auris* positive-selection culture medium comprising:
(a) a sugar, wherein the sugar is dextrose in the amount of 40 grams per liter of solvent;
(b) a yeast supplement, wherein the yeast supplement is Yeast Nitrogen Base in the amount of 6.7 grams per liter of solvent; and
(c) a Quaternary Ammonium Compound, wherein the Quaternary Ammonium Compound is at least one of the group consisting of cetylpyridinium chloride in the amount of 0.17 grams per liter of solvent, benzalkonium chloride in the amount of 0.26 grams per liter of solvent, and tetradecyltrimethylammonium bromide in the amount of 0.26 grams per liter of solvent.

2. A *Candida-auris* positive-selection culture medium comprising:
(a) a sugar, wherein the sugar is dextrose in the amount of 60 grams per liter of solvent;
(b) a yeast supplement, wherein the yeast supplement is Yeast Nitrogen Base in the amount of 6.7 grams per liter of solvent;
(c) a Quaternary Ammonium Compound, wherein the Quaternary Ammonium Compound is a blend of benzalkonium chloride in the amount of 70 milligrams per liter of solvent and tetradecyltrimethylammonium bromide in the amount of 80 milligrams per liter of solvent; and
(d) an antibiotic, wherein the antibiotic is chloramphenicol in the amount of 25 milligrams chloramphenicol per liter of solvent.

3. A *Candida-auris* positive-selection culture medium comprising:
(a) a sugar, wherein the sugar is dextrose in the amount of 60 grams per liter of solvent;
(b) a yeast supplement, wherein the yeast supplement is peptone in the amount of 10 grams per liter of solvent;
(c) a Quaternary Ammonium Compound, wherein the Quaternary Ammonium Compound is benzalkonium chloride in the amount of 130 milligrams per liter of solvent; and
(d) an antibiotic, wherein the antibiotic is chloramphenicol in the amount of 25 milligrams chloramphenicol per liter of solvent.

4. A culture medium comprising:
(a) a yeast growth medium; and
(b) a means for differentiating the growth of *Candida auris* relative to the growth of other species of fungi by suppressing the growth of other species of fungi relative to *Candida auris.*

5. A culture medium comprising:
(a) a sugar;
(b) a yeast supplement; and
(c) a Quaternary Ammonium Compound in an amount sufficient to suppress the growth of a species of fungi other than *Candida auris* relative to *Candida auris.*

6. The culture medium of claim 5 further comprising a solidifying agent.

7. The culture medium of claim 5 wherein the Quaternary Ammonium Compound is at least one of the group consisting of cetylpyridinium chloride, benzalkonium chloride, benzethonium chloride, and tetradecyltrimethylammonium bromide.

8. The culture medium of claim 5 wherein the yeast supplement is a nutritionally poor and defined supplement mixture.

9. The culture medium of claim 5 wherein the yeast supplement is a nutritionally rich and complex supplement mixture.

10. The culture medium of claim 5 further comprising an antibiotic.

11. The culture medium of claim 8 wherein the yeast supplement is Yeast Nitrogen Base without amino acids and with ammonium sulfate.

12. The culture medium of claim 9 wherein the yeast supplement is peptone.

13. The culture medium of claim 5 wherein the Quaternary Ammonium Compound suppresses the growth of a species of fungi other than *Candida auris* relative to *Candida auris* when inoculated and when incubated at a temperature in the range of 36.5° C.-39° C.

14. The culture medium of claim 5 wherein the Quaternary Ammonium Compound suppresses the growth of a species of fungi other than *Candida auris* relative to *Candida auris* when inoculated and when incubated at a temperature of at least 36.5° C.

15. The culture medium of claim 5 wherein the species of fungi other than *Candida auris* is at least one of the group consisting of *Candida glabrata, Candida krusei*, and *Saccharomyces cerevisiae.*

16. The culture medium of claim 5 wherein the species of fungi other than *Candida auris* is at least one of the group consisting of *Candida albicans, Candida famata, Candida haemulonii*, and *Candida duobushaemulonii.*

17. The culture medium of claim 5 wherein the species of fungi other than *Candida auris* is at least one of the group consisting of *Kodameae ohmeri, Candida lusitaniae, Candida parapsilosis*, and *Candida tropicalis.*

18. The culture medium of claim 14 wherein the species of fungi other than *Candida auris* is at least one of the group consisting of *Candida duobushaemulonii, Kodameae ohmeri, Candida haemulonii, Candida albicans, Candida krusei, Candida glabrata, Candida lusitaniae, Candida famata, Saccharomyces cerevisiae, Candida parapsilosis*, and *Candida tropicalis.*

* * * * *